US010897881B2

(12) United States Patent
Tyack

(10) Patent No.: US 10,897,881 B2
(45) Date of Patent: Jan. 26, 2021

(54) METHOD OF MAKING A CHICKEN WITH GERM CELLS EXPRESSING MARKER PROTEIN

(71) Applicants: Aviagen, Huntsville, AL (US); COMMONWEALTH SCIENTIFIC AND INDUSTRIAL RESEARCH ORGANISATION, Acton (AU)

(72) Inventor: Scott Geoffrey Tyack, Grovedale (AU)

(73) Assignees: Commonwealth Scientific and Industrial Research Organisation, Acton (AU); Aviagen, Huntsville, AL (US)

(*) Notice: Subject to any disclaimer, the term of this patent is extended or adjusted under 35 U.S.C. 154(b) by 0 days.

(21) Appl. No.: 14/394,712

(22) PCT Filed: Apr. 19, 2013

(86) PCT No.: PCT/AU2013/000414
§ 371 (c)(1),
(2) Date: Oct. 15, 2014

(87) PCT Pub. No.: WO2013/155572
PCT Pub. Date: Oct. 24, 2013

(65) Prior Publication Data
US 2015/0072064 A1 Mar. 12, 2015

Related U.S. Application Data

(60) Provisional application No. 61/783,823, filed on Mar. 14, 2013, provisional application No. 61/636,331, filed on Apr. 20, 2012.

(30) Foreign Application Priority Data

Apr. 12, 2013 (AU) ................. 2013204327

(51) Int. Cl.
C12N 15/00 (2006.01)
A01K 67/027 (2006.01)
C12N 15/873 (2010.01)
C12N 15/88 (2006.01)
C12N 15/89 (2006.01)
C12N 15/85 (2006.01)
C12N 15/90 (2006.01)
C12N 15/87 (2006.01)
C12N 15/113 (2010.01)

(52) U.S. Cl.
CPC ...... A01K 67/0275 (2013.01); A01K 67/0271 (2013.01); C12N 15/8509 (2013.01); C12N 15/873 (2013.01); C12N 15/88 (2013.01); C12N 15/89 (2013.01); C12N 15/902 (2013.01); A01K 2217/058 (2013.01); A01K 2227/30 (2013.01); A01K 2267/02 (2013.01); C12N 15/1131 (2013.01); C12N 15/87 (2013.01); C12N 2517/02 (2013.01); C12N 2800/90 (2013.01)

(58) Field of Classification Search
USPC ..................... 800/19, 21; 435/455
See application file for complete search history.

(56) References Cited

U.S. PATENT DOCUMENTS

| 5,162,215 A * | 11/1992 | Bosselman ........ A01K 67/0275 435/320.1 |
| 5,266,106 A | 11/1993 | Breton |
| 5,453,357 A | 9/1995 | Hogan |
| 7,241,574 B2 | 7/2007 | Choo et al. |
| 8,283,518 B2 * | 10/2012 | Cooper .............. A01K 67/0275 800/19 |
| 8,519,214 B2 * | 8/2013 | Ivarie .................. A01K 67/0275 800/19 |
| 2003/0069173 A1 | 4/2003 | Hawley-Nelson et al. |
| 2007/0004667 A1 | 1/2007 | McSwiggen et al. |
| 2007/0293449 A1 | 12/2007 | Kunyuan et al. |
| 2008/0188000 A1 * | 8/2008 | Reik .................... C07K 14/721 435/463 |
| 2012/0222143 A1 * | 8/2012 | Fahrenkrug ............ C12N 15/85 800/15 |
| 2013/0117870 A1 * | 5/2013 | Fahrenkrug ............ C12N 15/85 800/14 |

FOREIGN PATENT DOCUMENTS

| JP | 2003235558 | 8/2003 |
| WO | WO 1990/011355 | 10/1990 |
| WO | WO 1996/22321 | 7/1996 |
| WO | WO 1996/31549 | 10/1996 |
| WO | 1998/06437 | 2/1998 |
| WO | WO 1999/06533 | 2/1999 |
| WO | WO 1999/06534 | 2/1999 |
| WO | WO 2000/047717 | 8/2000 |
| WO | WO 2001/011018 | 2/2001 |
| WO | WO 2001/040477 | 11/2002 |
| WO | WO 2003/068960 | 8/2003 |

(Continued)

OTHER PUBLICATIONS

Thoroval (Transgenic Res. 1995, vol. 4, p. 369-376).*
Ono (Exp. Anim, 1995, vol. 44, No. 4, p. 275-278.*
Watanabe (Mol. Reprod. and Develop., 1994, vol. 38, No. 3, p. 268-274).*
Sun (Animal Sci. J. Apr. 2012, vol. 83, No. 4, p. 291-298, ePub Dec. 8, 2011).*
Lyall (Science, Jan. 14, 2011, vol. 331, No. 6014, p. 223-226.*
Kwon (Biol. Reprod. 2010, vol. 82, No. 6, p. 1057-1064).*
Porteus (Nature Biotech., 2005, vol. 23, No. 8, p. 967-973).*
High (Nature, 2005, vol. 435, p. 577 and 579) . Biotechnol., Jun. 2008, vol. 26, No. 6, p. 702-708).*

(Continued)

Primary Examiner — Michael C Wilson
(74) Attorney, Agent, or Firm — Gary J. Gershik

(57) ABSTRACT

The present invention relates to methods for transfecting cells. In particular, the present invention relates to methods of transfecting primordial germ cells in avians, and to methods of breeding avians with modified traits.

8 Claims, 8 Drawing Sheets

Specification includes a Sequence Listing.

(56) References Cited

FOREIGN PATENT DOCUMENTS

| WO | WO 2004/094627 | 11/2004 |
|---|---|---|
| WO | WO 2006/084035 | 10/2006 |
| WO | 2007/017759 | 2/2007 |
| WO | 2008/138072 | 11/2008 |
| WO | 2011/019385 | 2/2011 |

OTHER PUBLICATIONS

Ramirez ("Unexpected failure rates for modular assembly of engineered zinc fingers" Nature Methods, 2008, 5(5): 374-375).*
Huang (Nat. Biotechnol., Aug. 2011, vol. 29, No. 8, p. 699-700).*
Sander (Methods in Cell Biol. 2011, vol. 104, p. 51-58).*
Dong (PLoS ONE, Dec. 2011, vol. 6, No. 12, p. e28897).*
Bedell (Nature, Nov. 1, 2012, vol. 49, No. 7422, p. 114-118).*
Flisikowska, ("Efficient immunoglobulin gene disruption and targeted replacement in rabbit using zinc finger nucleases." 2011, PLoS ONE 6: e21045).*
Geurts (Science, Jul. 24, 2009, vol. 325, p. 433).*
Carlson (Transgenic Res., Jan. 9, 2011, p. 1-13).*
Carlson (Transgenic Res., Aug. 2012, vol. 21, No. 4, p. 901-902, Meeting date Aug. 7-10, 2011).*
Hauschild (PNAS, Sep. 6, 2011, vol. 108, No. 36, p. 12013-12017).*
Carlson (Mol. Therapy—Nucleic Acids, Jan. 24, 2012).*
Christian (Genetics, available online Jul. 26, 2008, vol. 186, p. 757-761).*
Li (Nature, Jul. 14, 2011, vol. 475, No. 7355, p. 217-221, plus Supplemental Material).*
Jinek (eLife, Jan. 2013, p. 1-9).*
Park ("piggyBac transposition into primordial germ cells is an efficient tool for transgenesis in chickens". PNAS, May 29, 2012 vol. 109, p. 9337-9341).*
Glover ("A Novel Piggybac Transposon Inducible Expression System Identifies a Role for AKT Signalling in Primordial Germ Cell Migration". PLoS ONE 8: e77222).*
Smith (J. Virol., Dec. 2013, vol. 87, No. 23, p. 12957-12966).*
Lyall (Science, Jan. 2011, vol. 331, p. 223-226).*
Balciunas et al. (2006) "Harnessing a High Cargo-Capacity Transposon for Genetic Applications in Vertebrates," PLoS Genet., 11:2:1716-1724.
Barrangou (2012) "RNA-mediated programmable DNA cleavage," Nature Biotechnology, 30:836-838.
Cong et al. (2013) "Multiplex Genome Engineering Using CRISPR/Cas Systems," Science, 339:819-823.
Davis and Stokoe (2010) "RZeviniewc Finger Nucleases as tools to understand and treat human diseases," BMC Med, 8:42.
Ding et al. (2005) "Efficient Transposition of the piggyBac (PB) Transposon in Mammalian Cells and Mice," Cell, 122:473-483.
Durai et al. (2005) "Zinc finger nucleases: custom-designed molecular scissors for genome engineering of plant and mammalian cells," Nucleic Acids Res, 33:5978-5990.
Floch et al (1997) "Cationic Phosphonolipids as non Viral Vectors for DNA Transfection in Hematopoietic Cell Lines and CD34+ Cells," Blood Cells, Molecules, and Diseases, 23:5:69-87.
Haensler and Szoka, (1993) "Polyamidoamine Cascade Polymers Mediate Efficient Transfection of Cells in Culture," Bioconjugate Chem, 4:372-379.
Hamburger and Hamilton (1951) "A Series of Normal Stages in the Development of the Chick Embryo," J Morphol, 88:49-92.
Han et al (2002) "Production of germline Chimeras by Transfer of Chicken Gonadal Primordial Germ Cells Maintained inVitro for an Extended Period," Theriogenology 58:1531-1539.
Hofland et al (1996) "Formation of Stable Cationic Lipid/DNA Complexes for Gene Transfer," Proc. Natl. Acad. Sci. USA, 93:7305-7309.
Ivics et al. (1997) "Molecular Reconstruction of Sleeping Beauty, a Tc1-like Transposon from Fish, and Its Transposition in Human Cells," Cell, 91:501-510.

Jeong et al (2002) "Simple Separation of Chicken Gonadal Primordial Germ Cells With and Without Foreign Genes," Cell Biology International, 26:7:647-651.
Jung et al (2005) "Development of Novel Markers for the Characterization of Chicken Primordial Germ Cells," Stem Cells, 23:689-698.
Kagami et al. (1997) "The Developmental Origin of Primordial Germ Cells and the Transmission of the Donor-Derived Gametes in Mixed-Sex Germline Chimeras to the Offspring in the Chicken," Mol Reprod Dev, 48:501-510.
Kawakami et al. (2000) "Identification of a functional transposase of the Tol2 element, an Ac-like element from the Japanese medaka fish, and its transposition in the zebrafish germ lineage," Proc Natl Acad Sci USA, 97:11403-11408.
Kwon et al., (2010) "Production of Biofunctional Recombinant Human Interleukin 1 Receptor Antagonist (rhIL1RN) from Transgenic Quail Egg White," Biology of Reproduction, 82:1057-1064.
Lyall et al., (2011) "Suppression of Avian Influenza Transmission in Genetically Modified Chickens," Science Mag. 331:223-226.
Naito, M., T. Harumi, Y. Matsubara, and T. Kuwana. "Evidence of in vivo transfection of circulating primordial germ cells in chickens." In EPC 2006—12th European Poultry Conference, Verona, Italy, Sep. 10-14, 2006. World's Poultry Science Association (WPSA), 2006.
Ono et al. (1995) "Gene Transfer into Circulation Primordial Germ Cells of Quail Embryos," Exp. Anim, 44:4:275-278.
Park et al (2003) "Birth of Germline Chimeras by Transfer of Chicken Embryonic Germ (EG) Cells Into Recipient Embryos," Molecular Reproduction and Development 35:389-395.
Park et al (2003) "Improved Germline Transmission in Chicken Chimeras Produced by Transplantation of Gonadal Primordial Germ Cells into Recipient Embryos," Biology of Reproduction, 68:1657-1662.
Petitte (2002) "The Avian Germline and Strategies for the Production of Transgenic Chickens," J Poultry Sci, 39:205-228.
Petitte and Modziak (2007) "The Incredible, Edible, and Therapeutic Egg," Proc Natl Acad Sci USA, 104:1739-1740.
Sullenger et al. (1990) "Overexpression of TAR Sequences Renders Cells Resistant to Human Immunodeficiency Virus Replication" Cell, 63:601-608.
Sun et al. (2012) "Transgenic Chimera Quial Production by Microinjecting Lentiviral Vecotr into the Blood Vessel of the Early Embryo," Animal Science Journal, 83:291-298.
Tang et al. (1996) "In Vitro Gene Delivery by Degraded Polyamidoamine Dendrimers," Bioconjugate Chem, 7:703-714.
Watanabe et al. (1994) "Liposome-Mediated DNA Transfer Into Chicken Primordial Germ Cells In Vivo," Molecular Reproduction and Development, 38:268-274.
Zhang et al. (2011) "Programmable Sequence-Specific Transcriptional Regulation of Mammalian Genome Using Designer TAL Effectors," Nature Biotechnology, 29:149-153.
Gonzales-Moran, (2011) "Histological and Stereological Changes in Growing and Regressing Chicken Ovaries During Development", The Anatomical Record, 294:893-904.
Oishi, et al. "Improvement of Transfection Efficiency in Cultured Chicken Primordial Germ Cells by Percoll Density Gradient Centrifugation," Bioscience, Biotechnology, and Biochemistry, 74(12), 2426-2430, 2010.
Hwang et al., (2013) "Efficient genome editing in zebrafish using a CRISPR-Cas system", nature biotechnology, 31(3):227-229.
Macdonald et al. (2012) "Efficient genetic modification and germline transmission of primordial germ cells using piggyBac and Tol2 transposons" Proceedings of The National Academy of Sciences. 109(23):E1466-E1472.
Naito et al. (2007) "Intense expression of GFP gene in gonads of chicken embryos by transfecting circulating primordial germ cells in vitro and in vivo". Journal of Poultry Science. 44(4):416-425.
Sato et al. (2007) "Stable integration and conditional expression of electroporated transgenes in chicken embryos" Developmental Biology. 305(2):616-624.

(56) References Cited

OTHER PUBLICATIONS

Tyack et al. (2013) "A new method for producing transgenic birds via direct in vivo transfection of primordial germ cells" Transgenic Research. 22(6):1257-1264.

* cited by examiner

```
                         SEQUENCE LISTING

<160> NUMBER OF SEQ ID NOS: 10

<210> SEQ ID NO 1
<211> LENGTH: 4090
<212> TYPE: DNA
<213> ORGANISM: Artificial Sequence
<220> FEATURE:
<223> OTHER INFORMATION: EGFP expression construct flanked by Tol2
      sequences

<400> SEQUENCE: 1
cagaggtgta aagtacttga gtaattttac ttgattactg tacttaagta ttattttgg      60 ggattttac  tttacttgag tacaattaaa aatcaatact tttacttta  cttaattaca   120 ttttttaga  aaaaaagta  cttttactc  cttacaattt tatttacagt caaaaagtac   180
ttattttttg gagatcactt cattctattt tcccttgcta ttaccaaacc aattgaattg   240
cgctgatgcc cagtttaatt taaatgttat ttattctgcc tatgaaaatc gttttcacat   300
tatatgaaat tggtcagaca tgttcattgg tcctttggaa gtgacgtcat gtcacatcta   360
ttaccacaat gcacagcacc ttgacctgga aattagggaa attataacag tcaatcagtg   420
gaagaaaatg gaggaagtat gtgattcatc agcagctgcg agcagcacag tccaaaatca   480
gccacaggat caagagcacc cgtggccgta tcttcgcaga tcgacattga ttattgacta   540
gttattaata gtaatcaatt acggggtcat tagttcatag cccatatatg gagttccgcg   600
ttacataact tacggtaaat ggcccgcctg gctgaccgcc caacgacccc cgcccattga   660
cgtcaataat gacgtatgtt cccatagtaa cgccaatagg gactttccat tgacgtcaat   720
gggtggagta tttacggtaa actgcccact tggcagtaca tcaagtgtat catatgccaa   780
gtacgccccc tattgacgtc aatgacggta aatggcccgc ctggcattat gcccagtaca   840
tgaccttatg ggactttcct acttggcagt acatctacgt attagtcatc gctattacca   900
tgggtcgagg tgagccccac gttctgcttc actctcccca tctccccccc ctccccaccc   960
ccaattttgt atttatttat ttttaatta tttttgtgcag cgatggggc gggggggggg  1020 ggggcgcgcg ccaggcgggg cggggcgggg cgagggcgg ggcggggcga ggcggagagg  1080
```

```
tgcggcggca gccaatcaga gcggcgcgct ccgaaagttt cctttattgg cgaggcggcg      1140
gcggcggcgg ccctataaaa agcgaagcgc gcggcgggcg ggagtcgctg cgttgccttc      1200
gccccgtgcc ccgctccgcg ccgcctcgcg ccgcccgccc cggctctgac tgaccgcgtt      1260
actcccacag gtgagcgggc gggacggccc ttctcctccg ggctgtaatt agcgcttggt      1320
ttaatgacgg ctcgtttctt ttctgtggct gcgtgaaagc cttaaagggc tccgggaggg      1380
ccctttgtgc gggggggagc ggctcggggg gtgcgtgcgt gtgtgtgtgc gtggggagcg      1440
ccgcgtgcgg cccgcgctgc ccggcggctg tgagcgctgc gggcgcggcg cggggctttg      1500
tgcgctccgc gtgtgcgcga ggggagcgcg gccgggggcg gtgccccgcg gtgcgggggg      1560
gctgcgaggg gaacaaaggc tgcgtgcggg gtgtgtgcgt gggggggtga gcaggggtg       1620 tgggcgcggc ggtcgggctg taaccccccc ctgcaccccc ctccccgagt tgctgagcac      1680
ggcccggctt cgggtgcggg gctccgtgcg gggcgtggcg cggggctcgc cgtgccgggc      1740 gggggtggc ggcaggtggg ggtgccgggc ggggcggggc cgcctcgggc cggggagggc       1800 tcggggagg ggcgcggcgg ccccggagcg ccggcggctg tcgaggcgcg gcgagccgca       1860
gccattgcct tttatggtaa tcgtgcgaga gggcgcaggg acttcctttg tcccaaatct      1920
ggcggagccg aaatctggga ggcgccgccg caccccctct agcgggcgcg gggcgaagcg      1980
gtgcggcgcc ggcaggaagg aaatgggcgg ggagggcctt cgtgcgtcgc cgcgccgccg      2040
tccccttctc cctctccagc ctcggggctg tccgcggggg gacggctgcc ttcgggggg       2100 acggggcagg gcggggttcg gcttctggcg tgtgaccggc ggctctagag cctctgctaa      2160
ccatgttcat gccttcttct ttttcctaca gctcctgggc aacgtgctgg ttattgtgct      2220
gtctcatcat tttggcaaag aattgtacca ccatggtgag caagggcgag gagctgttca      2280
ccggggtggt gcccatcctg gtcgagctgg acggcgacgt aaacggccac aagttcagcg      2340
tgtccggcga gggcgagggc gatgccacct acggcaagct gaccctgaag ttcatctgca      2400
ccaccggcaa gctgcccgtg ccctggccca cactagtgac caccttcgct tacggcgtgc      2460
agtgcttcag ccgctacccc gaccacatga agcagcacga cttcttcaag tccgccatgc      2520
ccgaaggcta cgtccaggag cgcaccatct tcttcaagga cgacggcaac tacaagaccc      2580
gcgccgaggt gaagttcgag ggcgacaccc tggtgaaccg catcgagctg aagggcatcg      2640
acttcaagga ggacggcaac atcctggggc acaagctgga gtacaacttc aacagccaca      2700
acgtatacat catggccgac aagcagaaga cggcatcaa ggtgaacttc aagatccgcc       2760
acaacatcga ggacggcagc gtgcagctcg ccgaccacta ccagcagaac ccccccatcg      2820
gcgacggccc cgtgctgctg cccgacaacc actacctgag cacccagtcc gccctgagca      2880
aagaccccaa cgagaagcgc gatcacatgg tcctgctgga gttcgtgacc gccgccggga      2940
tcactcacgg catggacgag ctgtacaagt agggcggctc gaggatatca ggatcaattc      3000
actcctcagg tgcaggctgc ctatcagaag gtggtggctg gtgtggccaa tgccctggct      3060
cacaaatacc actgagatct tttccctct gccaaaaatt atgggacat catgaagccc        3120 cttgagcatc tgacttctgg ctaataaagg aaatttattt tcattgcaat agtgtgttgg      3180
aattttttgt gtctctcact cggaaggaca tatgggaggg caaatcattt aaaacatcag      3240
aatgagtatt tggtttagag tttggcaaca tatgcccata tgctggctgc catgaacaaa      3300
ggttggctat aaagaggtca tcagtatatg aaacagcccc ctgctgtcca ttccttattc      3360
catagaaaag ccttgacttg aggttagatt ttttttatat tttgttttgt gttatttttt      3420 tcttttaacat ccctaaaatt ttccttacat gttttactag ccagattttt cctcctctcc      3480
```

```
tgactactcc cagtcatagc tgtccctctt ctcttatgga gatccctcga cctgcagccc    3540
aagctcgagg gcccatctgg cctgtgtttc agacaccagg gagtctctgc tcacgtttcc    3600
tgctatttgc agcctctcta tcaagactaa tacacctctt cccgcatcgg ctgcctgtga    3660
gaggcttttc agcactgcag gattgctttt cagcccaaaa agagctaggc ttgacactaa    3720
caattttgag aatcagcttc tactgaagtt aaatctgagg ttttacaact ttgagtagcg    3780
tgtactggca ttagattgtc tgtcttatag tttgataatt aaatacaaac agttctaaag    3840
caggataaaa ccttgtatgc atttcattta atgttttttg agattaaaag cttaaacaag    3900
aatctctagt tttctttctt gcttttactt ttacttcctt aatactcaag tacaatttta    3960
atggagtact tttttacttt tactcaagta agattctagc cagatacttt tacttttaat    4020
tgagtaaaat tttccctaag tacttgtact ttcacttgag taaaatttt gagtactttt    4080 tacacctctg                                                           4090
```

<210> SEQ ID NO 2
<211> LENGTH: 706
<212> TYPE: PRT
<213> ORGANISM: Artificial Sequence
<220> FEATURE:
<223> OTHER INFORMATION: Sequence encoding Tol2 transposase

<400> SEQUENCE: 2

```
Met Phe Met Pro Ser Ser Phe Ser Tyr Ser Ser Trp Ala Thr Cys Trp
  1               5                  10                  15

Leu Leu Cys Cys Leu Ile Ile Leu Ala Lys Asn Ser Ser Arg Ser Ser
             20                  25                  30

His Ile Tyr Tyr His Asn Ala Gln His Leu Asp Leu Glu Ile Arg Glu
         35                  40                  45

Ile Ile Thr Val Asn Gln Trp Lys Lys Met Glu Glu Val Cys Asp Ser
     50                  55                  60

Ser Ala Ala Ala Ser Ser Thr Val Gln Asn Gln Pro Gln Asp Gln Glu
 65                  70                  75                  80

His Pro Trp Pro Tyr Leu Arg Glu Phe Phe Ser Leu Ser Gly Val Asn
                 85                  90                  95

Lys Asp Ser Phe Lys Met Lys Cys Val Leu Cys Leu Pro Leu Asn Lys
            100                 105                 110

Glu Ile Ser Ala Phe Lys Ser Ser Pro Ser Asn Leu Arg Lys His Ile
        115                 120                 125

Glu Arg Met His Pro Asn Tyr Leu Lys Asn Tyr Ser Lys Leu Thr Ala
    130                 135                 140

Gln Lys Arg Lys Ile Gly Thr Ser Thr His Ala Ser Ser Ser Lys Gln
145                 150                 155                 160

Leu Lys Val Asp Ser Val Phe Pro Val Lys His Val Ser Pro Val Thr
                165                 170                 175

Val Asn Lys Ala Ile Leu Arg Tyr Ile Ile Gln Gly Leu His Pro Phe
            180                 185                 190

Ser Thr Val Asp Leu Pro Ser Phe Lys Glu Leu Ile Ser Thr Leu Gln
        195                 200                 205

Pro Gly Ile Ser Val Ile Thr Arg Pro Thr Leu Arg Ser Lys Ile Ala
    210                 215                 220

Glu Ala Ala Leu Ile Met Lys Gln Lys Val Thr Ala Ala Met Ser Glu
225                 230                 235                 240

Val Glu Trp Ile Ala Thr Thr Thr Asp Cys Trp Thr Ala Arg Arg Lys
```

```
                        245                 250                 255
Ser Phe Ile Gly Val Thr Ala His Trp Ile Asn Pro Gly Ser Leu Glu
                260                 265                 270

Arg His Ser Ala Ala Leu Ala Cys Lys Arg Leu Met Gly Ser His Thr
            275                 280                 285

Phe Glu Val Leu Ala Ser Ala Met Asn Asp Ile His Ser Glu Tyr Glu
        290                 295                 300

Ile Arg Asp Lys Val Val Cys Thr Thr Thr Asp Ser Gly Ser Asn Phe
305                 310                 315                 320

Met Lys Ala Phe Arg Val Phe Gly Val Glu Asn Asn Asp Ile Glu Thr
                325                 330                 335

Glu Ala Arg Arg Cys Glu Ser Asp Asp Thr Asp Ser Glu Gly Cys Gly
            340                 345                 350

Glu Gly Ser Asp Gly Val Glu Phe Gln Asp Ala Ser Arg Val Leu Asp
        355                 360                 365

Gln Asp Asp Gly Phe Glu Phe Gln Leu Pro Lys His Gln Lys Cys Ala
    370                 375                 380

Cys His Leu Leu Asn Leu Val Ser Ser Val Asp Ala Gln Lys Ala Leu
385                 390                 395                 400

Ser Asn Glu His Tyr Lys Lys Leu Tyr Arg Ser Val Phe Gly Lys Cys
                405                 410                 415

Gln Ala Leu Trp Asn Lys Ser Ser Arg Ser Ala Leu Ala Ala Glu Ala
            420                 425                 430

Val Glu Ser Glu Ser Arg Leu Gln Leu Leu Arg Pro Asn Gln Thr Arg
        435                 440                 445

Trp Asn Ser Thr Phe Met Ala Val Asp Arg Ile Leu Gln Ile Cys Lys
    450                 455                 460

Glu Ala Gly Glu Gly Ala Leu Arg Asn Ile Cys Thr Ser Leu Glu Val
465                 470                 475                 480

Pro Met Phe Asn Pro Ala Glu Met Leu Phe Leu Thr Glu Trp Ala Asn
                485                 490                 495

Thr Met Arg Pro Val Ala Lys Val Leu Asp Ile Leu Gln Ala Glu Thr
            500                 505                 510

Asn Thr Gln Leu Gly Trp Leu Leu Pro Ser Val His Gln Leu Ser Leu
        515                 520                 525

Lys Leu Gln Arg Leu His His Ser Leu Arg Tyr Cys Asp Pro Leu Val
    530                 535                 540

Asp Ala Leu Gln Gln Gly Ile Gln Thr Arg Phe Lys His Met Phe Glu
545                 550                 555                 560

Asp Pro Glu Ile Ile Ala Ala Ala Ile Leu Leu Pro Lys Phe Arg Thr
                565                 570                 575

Ser Trp Thr Asn Asp Glu Thr Ile Ile Lys Arg Gly Met Asp Tyr Ile
            580                 585                 590

Arg Val His Leu Glu Pro Leu Asp His Lys Lys Glu Leu Ala Asn Ser
        595                 600                 605

Ser Ser Asp Asp Glu Asp Phe Phe Ala Ser Leu Lys Pro Thr Thr His
    610                 615                 620

Glu Ala Ser Lys Glu Leu Asp Gly Tyr Leu Ala Cys Val Ser Asp Thr
625                 630                 635                 640

Arg Glu Ser Leu Leu Thr Phe Pro Ala Ile Cys Ser Leu Ser Ile Lys
                645                 650                 655

Thr Asn Thr Pro Leu Pro Ala Ser Ala Ala Cys Glu Arg Leu Phe Ser
            660                 665                 670
```

```
Thr Ala Gly Leu Leu Phe Ser Pro Lys Arg Ala Arg Leu Asp Thr Asn
        675                 680                 685

Asn Phe Glu Asn Gln Leu Leu Lys Leu Asn Leu Arg Phe Tyr Asn
        690                 695                 700

Phe Glu
705

<210> SEQ ID NO 3
<211> LENGTH: 20
<212> TYPE: DNA
<213> ORGANISM: Artificial Sequence
<220> FEATURE:
<223> OTHER INFORMATION: Screen 7 oligonucleotide primer

<400> SEQUENCE: 3
gtgactcaga ctcctgttag                                            20

<210> SEQ ID NO 4
<211> LENGTH: 20
<212> TYPE: DNA
<213> ORGANISM: Artificial Sequence
<220> FEATURE:
<223> OTHER INFORMATION: Screen 6 oligonucleotide primer

<400> SEQUENCE: 4
tctgctgctt cacagtcttc                                            20

<210> SEQ ID NO 5
<211> LENGTH: 33
<212> TYPE: DNA
<213> ORGANISM: Artificial Sequence
<220> FEATURE:
<223> OTHER INFORMATION: miniTol2 forward oligonucleotide primer

<400> SEQUENCE: 5
cagtcaaaaa gtacttattt tttggagatc act                             33

<210> SEQ ID NO 6
<211> LENGTH: 21
<212> TYPE: DNA
<213> ORGANISM: Artificial Sequence
<220> FEATURE:
<223> OTHER INFORMATION: miniTol2 Reverse oligonucleotide primer

<400> SEQUENCE: 6
gggcatcagc gcaattcaat t                                          21

<210> SEQ ID NO 7
<211> LENGTH: 17
<212> TYPE: DNA
<213> ORGANISM: Artificial Sequence
<220> FEATURE:
<223> OTHER INFORMATION: miniTol2 detection probe

<400> SEQUENCE: 7
atagcaaggg aaaatag                                               17

<210> SEQ ID NO 8
<211> LENGTH: 21
<212> TYPE: DNA
<213> ORGANISM: Artificial Sequence
<220> FEATURE:
<223> OTHER INFORMATION: Genomic control region forward primer

<400> SEQUENCE: 8
```

```
gatgggaaaa ccctgaacct c                                              21

<210> SEQ ID NO 9
<211> LENGTH: 26
<212> TYPE: DNA
<213> ORGANISM: Artificial Sequence
<220> FEATURE:
<223> OTHER INFORMATION: Genomic region control reverse primer

<400> SEQUENCE: 9
caacctgcta gagaagatga gaagag                                         26

<210> SEQ ID NO 10
<211> LENGTH: 15
<212> TYPE: DNA
<213> ORGANISM: Artificial Sequence
<220> FEATURE:
<223> OTHER INFORMATION: Genomic control region oligonucleotide probe

<400> SEQUENCE: 10
ctgcactgaa tggac                                                     15
```

METHOD OF MAKING A CHICKEN WITH GERM CELLS EXPRESSING MARKER PROTEIN

FIELD OF THE INVENTION

The present invention relates to methods for transfecting cells. In particular, the present invention relates to methods of transfecting primordial germ cells in avians, and to methods of breeding avians with modified traits.

BACKGROUND

The development of an efficient technique to develop transgenic or genetically modified avians is of major importance to both the agriculture and biopharmacy industries, as well as increasing our understanding of avian biology via functional genomics studies. Poultry production will play a major role in ensuring food security for the planet in the face of population growth, and modern advances in biotechnology such as the development of transgenic poultry will help the industry to meet the demand for increased production.

More specifically, the application of transgenic technology to modify traits in poultry that are not possible through conventional breeding, such as disease resistance and modulation of sex determination, will now be possible and provide major benefits to the poultry industry. The demand for biopharmaceutical proteins is rapidly growing and until recently in vitro cell-based manufacturing systems to produce new recombinant proteins for the treatment of disease have been used. The use of transgenic livestock as bioreactors for recombinant protein production is now being developed as a major alternative to expensive and labour intensive cell-based systems. The development of transgenic technology for the chicken has enabled the egg to be developed as a bioreactor for high levels of production and purification of biopharmaceutical proteins.

Attempts were also made to introduce selected foreign genes by cloning them into a retrovirus vector (e.g. reticuloendothelial virus or avian leukosis virus), injecting the recombinant virus into fertile eggs, allowing the virus to infect the developing embryo (e.g. primordial germ cells) thereby creating a chimeric gonad or ova, and using the resultant recombinant to try to introduce a foreign gene into the progeny. However, the poultry industry has been reluctant to commercially use this technology as the virus (in its natural state) is a pathogen, even variant replication competent virus vectors can sometimes induce tumors, and replication incompetent variants require high or repeated dosages. Also, even replication defective virus constructs can pose some risk of recombining with endogenous virus envelope and becoming replication competent. Further, these vectors are currently limited to DNA inserts of relatively small size (e.g. two kilobases or less).

There have also been attempts to inject foreign DNA into the undeveloped fertilized ovum after it is surgically removed from the hen. However, this approach required incubating the developing embryo in a series of surrogate containers. Further, it required specialized laying flocks and extensive practice to obtain the needed surgical and technical skills.

An alternative approach involves the injection of genetically modified embryonic cells or primordial germ cells (PGCs) into a recipient embryo shortly after lay. In this approach PCG cultures were created which retained their ability to differentiate into functional ova or spermatozoa producing cells when incorporated into the developing embryo. PGC cultures of this type can be genetically modified and then injected into recipient embryos. The recipient embryos would typically have been modified by gamma irradiation to debilitate the endogenous primordial germ cells so as to give the injected cells a selection advantage in homing into the gonadal ridge. The modified cells would then mature and produce spermatozoa or ova capable of transmitting the transgene to at least the next generation. This technique is time consuming, however, as it requires the removal of PGCs from a donor embryo, and their subsequent culture and reintroduction into a recipient embryo. Furthermore, the efficiency at which avians comprising genetically modified PGCs can be obtained using this technique is low.

Accordingly, there remains a need for methods of genetically modifying avian primordial germ cells.

SUMMARY OF THE INVENTION

The present inventors have found that the direct injection of transfection reagents mixed with DNA into the blood of developing avian embryos results in the DNA being introduced into primordial germ cells (PGCs) and insertion of the DNA into the genome of the avian.

Accordingly, the present invention provides a method for producing an avian comprising genetically modified germ cells, the method comprising:
(i) injecting a transfection mixture comprising a polynucleotide mixed with a transfection reagent into a blood vessel of an avian embryo,
whereby the polynucleotide is inserted into the genome of one or more germ cells in the avian.

In one embodiment, the method further comprises (ii) incubating the embryo at a temperature sufficient for the embryo to develop into a chick.

The transfection mixture is preferably injected into the avian embryo at the time of PGC migration at approximately Stages 12-17. In one preferred embodiment, the transfection mixture is injected into the avian embryo at Stages 13-14.

Although any suitable transfection reagent may be used in the methods of the invention, preferably the transfection reagent comprises a cationic lipid.

In one embodiment, the transfection reagent comprises a monovalent cationic lipid selected from one or more of DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide) and DDAB (dimethyl dioctadecyl ammonium bromide).

In another embodiment, the transfection reagent comprises a polyvalent cationic lipid selected from one or more of DOSPA (2,3-dioleyloxy-N-[2(sperminecarboxamido) ethyl]-N,N-dimethyl-1-propanaminium trifluoroacetate) and DOSPER (1,3-dioleoyloxy-2-(6carboxy spermyl)-propyl-amid, TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldioleyl spermine).

In yet another embodiment, the transfection reagent comprises DOSPA (2,3-dioleyloxy-N-[2(sperminecarboxamido) ethyl]-N,N-dimethyl-1-propanaminium trifluoroacetate).

In another embodiment, the transfection reagent further comprises a neutral lipid. The neutral lipid may comprise, for example, (DOPE) dioleoyl phosphatidylethanolamine, DPhPE (diphytanoylphosphatidylethanolamine) or cholesterol.

In one particular embodiment, the transfection reagent comprises a 3:1 (w/w) mixture of DOSPA and DOPE prior to mixture of the transfection reagent with the polynucleotide.

Advantageously, the methods of the present invention are suited to the use of non-retroviral methods of introducing a polynucleotide into the genome of a germ cell. Thus, in one embodiment, the polynucleotide further comprises a nucleotide sequence encoding a transposon or zinc finger nuclease.

In one particular embodiment, the transfection mixture comprises a polynucleotide encoding a transposase. The transposase may be encoded by DNA such as in a plasmid, or alternatively the polynucleotide encoding the transposase is RNA.

In one specific embodiment, the transposon is selected from Tol2, mini-Tol2, Sleeping Beauty and PiggyBac.

In another embodiment, the polynucleotide comprises a sequence encoding a zinc finger nuclease.

While the germ cells that are genetically modified in the avian may be embryonic germ cells, preferably the cells are primordial germ cells.

In one embodiment, the injection mixture is injected into the embryo in the eggshell in which the embryo developed.

The polynucleotide in the transfection mixture may be an RNA molecule or DNA molecule that encodes a polypeptide, or a DNA molecule encoding an RNA comprising a double-stranded region. In one particular embodiment, the polynucleotide encodes an RNA molecule comprising a double-stranded region. The RNA molecule may be, for example, an siRNA, shRNA or RNA decoy.

In another embodiment, the polynucleotide encodes a polypeptide.

In one embodiment, the RNA molecule or polypeptide reduces replication of a virus in a cell compared to a cell lacking the RNA molecule or polypeptide.

The methods of the invention may be used to target any viral pathogen of an avian. In one embodiment, the virus is influenza virus.

The present invention further provides an avian comprising genetically modified germ cells, wherein the avian is produced by the method of the invention.

The present invention further provides a genetically modified germ cell of the avian of the invention, wherein the germ cell comprises the polynucleotide inserted into the genome.

The present invention further provides sperm produced by the avian comprising genetically modified cells of the invention.

The present invention further provides an egg produced by the avian comprising genetically modified cells of the invention.

The present invention further provides a method for genetically modifying germ cells in an avian, the method comprising
(i) injecting a transfection mixture comprising a polynucleotide mixed with a transfection reagent into a blood vessel of an avian embryo contained in an egg, and
(ii) incubating the embryo at a temperature sufficient to permit the embryo to develop into a chick, wherein the polynucleotide is inserted into the genome of one or more germ cells in the avian.

In additional embodiments, the method comprises one or more of the features of the invention as described herein.

The present invention further provides a method for producing a genetically modified avian, the method comprising:
(i) obtaining the avian comprising genetically modified germ cells of the invention,
(ii) breeding from the avian comprising genetically modified germ cells to produce progeny, and
(iii) selecting progeny comprising the polynucleotide inserted into the genome.

The present invention further provides a genetically modified avian produced by the method of the invention.

The present invention further provides a method of producing food, the method comprising:
(i) obtaining the avian comprising genetically modified germ cells of the invention or the genetically modified avian of the invention, and
(ii) producing food from the avian.

In one embodiment, the method comprises harvesting meat and/or eggs from the avian.

The present invention further provides a method of breeding a genetically modified avian, the method comprising:
(i) performing the method of the invention to produce a chick or progeny,
(ii) allowing the chick or progeny to develop into a sexually mature avian, and
(iii) breeding from the sexually mature avian to produce a genetically modified avian.

In one embodiment, the invention provides a genetically modified avian produced according to the method of the invention.

The present invention further provides a method of modulating a trait in an avian, the method comprising
(i) injecting a transfection mixture comprising a polynucleotide mixed with a transfection reagent into a blood vessel of an avian embryo, whereby the polynucleotide is inserted into the genome of one or more germ cells in the avian and
(ii) incubating the embryo at a temperature sufficient to permit the embryo to develop into a chick,
wherein the polynucleotide encodes a polypeptide or RNA molecule comprising a double-stranded region which modulates a trait in the avian.

In one embodiment, the RNA molecule comprises an siRNA, shRNA or RNA decoy.

In one embodiment, the trait is selected from muscle mass, sex, nutritional content and/or disease resistance.

The present invention further provides a method of increasing the resistance of an avian to a virus, the method comprising performing the method of the invention, wherein the polynucleotide is an siRNA, shRNA or RNA decoy that reduces replication of the virus in a cell, or the polynucleotide encodes an antiviral peptide that reduces replication of the virus in a cell.

In one particular embodiment, the virus is influenza virus.

The present invention further provides an avian produced according to the method of the invention.

In some embodiments of the invention, the avian is selected from a chicken, duck, turkey, goose, bantam or quail.

In another embodiment of the methods of the invention, the transfection mixture further comprises a targeting nuclease, or a polynucleotide encoding a targeting nuclease, to facilitate integration of the polynucleotide into the genome of the germ cell. For example, the targeting nuclease may be selected from a Zinc Finger Nuclease, TALEN and CRISPR.

The present invention further provides a method for producing an avian comprising genetically modified germ cells, the method comprising:
(i) injecting a transfection mixture comprising a polynucleotide mixed with a transfection reagent into a blood vessel of an avian embryo, whereby the polynucleotide is inserted into the genome of one or more germ cells in the avian, and (ii) incubating the embryo at a temperature sufficient for the embryo to develop into a chick, wherein the transfection reagent comprises a cationic lipid, the polynucleotide further comprises a sequence encoding a transposon, and the transfection mixture is injected into the blood vessel of the avian embryo at Stages 13-14.

In one embodiment, the transfection reagent comprises Lipofectamine 2000 or a 3:1 (w/w) mixture of DOSPA and DOPE prior to mixture of the transfection reagent with the polynucleotide, the transposon is Tol2 or mini-Tol2, and the transfection mixture comprises a polynucleotide encoding Tol2 transposase.

The present invention further provides a method for producing an avian comprising genetically modified germ cells, the method comprising:

(i) injecting a transfection mixture comprising a polynucleotide mixed with a transfection reagent into a blood vessel of an avian embryo, whereby the polynucleotide is inserted into the genome of one or more germ cells in the avian, and (ii) incubating the embryo at a temperature sufficient for the embryo to develop into a chick, wherein the transfection reagent comprises a cationic lipid and a neutral lipid, the polynucleotide further comprises a sequence encoding a zinc finger nuclease, and the transfection mixture is injected into the blood vessel of the avian embryo at Stages 13-14.

In one embodiment, the transfection reagent comprises Lipofectamine 2000 or a 3:1 (w/w) mixture of DOSPA and DOPE prior to mixture of the transfection reagent with the polynucleotide.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

KEY TO THE SEQUENCE LISTING

Figure 1:
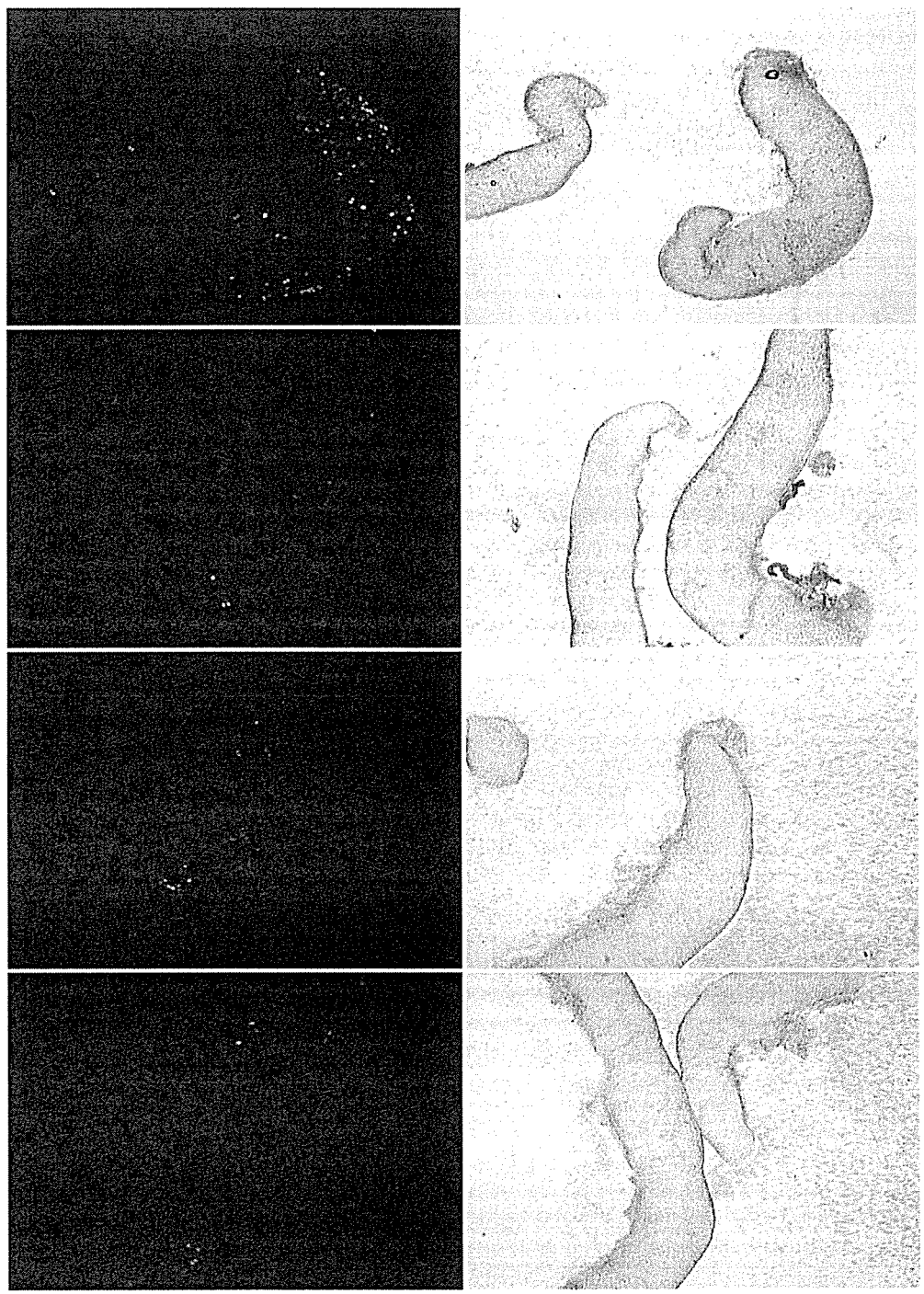
FIG. 1. Direct injection of DNA encoding EGFP complexed with Lipofectamine 2000 into avian embryos. Fluorescent (left side) and matching brightfield (right side) images of gonads removed from Day 7 embryos.

SEQ ID NO:1—Tol2 EGFP construct polynucleotide sequence
SEQ ID NO:2—Tol2 transposase amino acid sequence
SEQ ID NO:3—Screen 7 oligonucleotide primer
SEQ ID NO:4—Screen 6 oligonucleotide primer
SEQ ID NO:5—miniTol2 forward oligonucleotide primer
SEQ ID NO:6—miniTol2 reverse oligonucleotide primer
SEQ ID NO:7—miniTol2 detection probe
SEQ ID NO:8—Genomic control region forward primer
SEQ ID NO:9—Genomic control region reverse primer
SEQ ID NO:10—Genomic control region probe

DETAILED DESCRIPTION

General Techniques and Definitions

Unless specifically defined otherwise, all technical and scientific terms used herein shall be taken to have the same meaning as commonly understood by one of ordinary skill in the art (e.g., in protein chemistry, biochemistry, cell culture, molecular genetics, microbiology, and immunology).

Unless otherwise indicated, the recombinant DNA and protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "avian" as used herein refers to any species, subspecies *or* race of organism of the taxonomic Class Aves, such as, but not limited to, such organisms as chicken, turkey, duck, goose, quail, pheasants, parrots, finches, hawks, crows and ratites including ostrich, emu and cassowary. The term includes the various known strains of *Gallus gallus* (chickens), for example, White Leghorn, Brown Leghorn, Barred-Rock, Sussex, New Hampshire, Rhode Island, Australorp, Cornish, Minorca, Amrox, California Gray, Italian Partidge-coloured, as well as strains of turkeys, pheasants, quails, duck, ostriches and other poultry commonly bred in commercial quantities.

The term "poultry" includes all avians kept, harvested, or domesticated for meat or eggs, for example chicken, turkey, ostrich, game hen, squab, guinea fowl, pheasant, quail, duck, goose, and emu.

As used herein, a "genetically modified avian" or "transgenic avian" refers to any avian in which one or more of the cells of the avian contains heterologous nucleic acid introduced by way of human intervention.

Direct Injection Technique

The germline in chickens is initiated as cells from the epiblast of a Stage X embryo ingress into the nascent hypoblast (Kagami et al., 1997; and Petitte, 2002). As the hypoblast progresses anteriorly, the pre-primordial germ cells are swept forward into the germinal crescent where they can be identified as large glycogen laden cells. The earliest identification of cells in the germline by these morphological criteria is approximately 8 hours after the beginning of incubation (Stage 4 using the staging system established by Hamburger and Hamilton, (1951)). The primordial germ cells reside in the germinal crescent from Stage 4 until they migrate through the vasculature during Stage 12-17. At this time, the primordial germ cells are a small population of about 200 cells. From the vasculature, the primordial germ cells migrate into the genital ridge and are incorporated into the ovary or testes as the gonad differentiates.

Germline chimeric chickens have been generated previously by transplantation of donor PGCs and gonadal germ cells from various developmental stages (blastoderm to day 20 embryo) into recipient embryos. Methods of obtaining transgenic chickens from long-term cultures of avian primordial germ cells (PGCs) have also been described, for example, in US Patent Application 20060206952. When combined with a host avian embryo by known procedures, those modified PGCs are transmitted through the germline to yield genetically modified offspring.

In contrast to the commonly used prior art methods which rely on the harvesting of PGCs from donor embryos, the methods of the present invention involve the direct injection of a transfection mixture into an avian embryo. Thus, the methods of the invention may be used to transfect avian germ cells including PGCs and embryonic germ cells.

Transfection Mixture

In the methods of the present invention, a polynucleotide is complexed or mixed with a suitable transfection reagent. The term "transfection reagent" as used herein refers to a composition added to the polynucleotide for enhancing the uptake of the polynucleotide into a eukaryotic cell including, but not limited to, an avian cell such as a primordial germ cell. While any transfection reagent known in the art to be suitable for transfecting eukaryotic cells may be used, the present inventors have found that transfection reagents comprising a cationic lipid are particularly useful in the methods of the present invention. Thus, in a preferred embodiment, monovalent cationic lipids are selected from one or more of DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide) or DDAB (dimethyl dioctadecyl ammonium bromide). Preferred polyvalent cationic lipids are lipospermines, specifically DOSPA (2,3-dioleyloxy-N-[2(sperminecarboxamido) ethyl]-N,N-dimethyl-1-propanamin-ium trifluoroacetate) and DOSPER (1,3-dioleoyloxy-2-(6carboxy spermyl)-propyl-amid, and the di- and tetra-alkyl-tetra-methyl spermines, including but not limited to TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldioleyl spermine). Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. A cationic lipid composition composed of a 3:1 (w/w) mixture of DOSPA and DOPE or a 1:1 (w/w) mixture of DOTMA and DOPE are generally useful in the methods of the invention. Non-limiting examples of suitable commercially available transfection reagents comprising cationic lipids include Lipofectamine (Life Technologies) and Lipofectamine 2000 (Life Technologies).

In general, any dendrimer that can be employed to introduce nucleic acid into any cell, particularly into a eukaryotic cell, is useful in the methods of this invention. Dendrimers of generation 5 or higher (G5 or higher) are preferred, with those of generation between G5-G10 being of particular interest. Dendrimers that may be useful in the invention include those with $NH_3$ or ethylenediamine cores, $GX(NH_3)$ or GX(EDA), where X=the generation number. Dendrimers where X=5-10 being preferred. Dendrimers that may be useful in the invention include those in which the repeating unit of the internal layers is a amidoamine (to form polyamidoamines, i.e. PAMAMs). Useful dendrimers include those in which the terminal functional groups at the outer surface of the dendrimer provides a positive charge density, e.g., as with terminal amine functional groups. The surface charge and the chemical nature of the outer dendrimer surface can be varied by changing the functional groups on the surface, for example, by reaction of some or all of the surface amine groups. Of particular interest are dendrimers that are functionalized by reaction with cationic amino acids, such as lysine or arginine. Grafted dendrimers as described, for example in PCT applications WO 9622321 and WO9631549 and noted in U.S. Pat. No. 5,266,106, can be employed in methods of this invention. Activated dendrimers (Haensler and Szoka, 1993; and Tang et al., 1996) can also be employed in methods of the invention.

The transfection reagent may further comprise peptide sequences from viral, bacterial or animal proteins and other sources, including peptides, proteins or fragments or portions thereof that can enhance the efficiency of transfection of eukaryotic cells mediated by transfection agents, including cationic lipids and dendrimers. Such peptides are described in US 20030069173 and include, for example, viral peptides or proteins of influenza virus, adenovirus, Semliki forest virus, HIV, hepatitis, herpes simplex virus, vesicular stomatitis virus or simian virus 40 and more specifically an RGD-peptide sequence, an NLS peptide sequence and/or a VSVG-peptide sequence and to modified peptides or proteins of each of the foregoing.

The polynucleotide may be mixed (or "complexed") with the transfection reagent according to the manufacturers instructions or known protocols. By way of example, when transfecting plasmid DNA with Lipofectamine 2000 transfection reagent (Invitrogen, Life Technologies), DNA may be diluted in 50 μl Opit-MEM medium and mixed gently. The Lipofectamine 2000 reagent is mixed gently and an appropriate amount diluted in 50 μl Opti-MEM medium. After a 5 minute incubation, the diluted DNA and transfection reagent are combined and mixed gently at room temperature for 20 minutes.

A suitable volume of the transfection mixture may then be directly injected into an avian embryo in accordance with the method of the invention. Typically, a suitable volume for injection into an avian embryo is about 1 μl to about 3 μl, although suitable volumes may be determined by factors such as the stage of the embryo and species of avian being injected. The person skilled in the art will appreciate that the protocols for mixing the transfection reagent and DNA, as well as the volume to be injected into the avian embryo, may be optimised in light of the teachings of the present specification.

Injection into the Embryo

Prior to injection, eggs are incubated at a suitable temperature for embryonic development, for example around 37.5 to 38° C., with the pointy end (taglion) upward for approximately 2.5 days (Stages 12-17), or until such time as the blood vessels in the embryo are of sufficient size to allow injection. The optimal time for injection of the transfection mixture is the time of PGC migration that typically occurs around Stages 12-17, but more preferably Stages 13-14. As the person skilled in the art will appreciate, broiler line chickens typically have faster growing embryos, and so injection should preferably occur early in Stages 13-14 so as to introduce the transfection mixture into the bloodstream at the time of PGC migration.

To access a blood vessel of the avian embryo, a hole is made in the egg shell. For example, an approximately 10 mm hole may be made in the pointy end of the egg using a suitable implement such as forceps. The section of shell and associated membranes are carefully removed while avoiding injury to the embryo and it's membranes.

Micropipettes made of siliconized glass capillary tubing may be used to inject the transfection mixture into the blood vessel of the avian embryo. Typically, micropipettes are drawn out or "pulled" with a micropipette puller and the tips bevelled with the aid of a pipette grinder to a diameter (internal opening) of approximately 10 μm to about 50 μm diameter, more preferably around 25 μm to around 30 μm in diameter. Micropipettes are typically ground to a diameter of around 25 μm to around 30 μm to facilitate the injection of PGCs into an avian embryo. The skilled person will appreciate that a narrower diameter may be used in the methods of the present invention as the transfection mixture does not comprise cells. A micropipette produced in this manner is also referred to as a "pulled glass capillary".

A pulled glass capillary is loaded with approximately 1-3 μm of the transfection complex. The injection is made into any blood vessel of sufficient size to accommodate the capillary, such as the marginal vein or the dorsal aorta, or any another blood vessel of sufficient size to take the capillary. Air pressure may be used to expel the transfection complex from the capillary into the blood vessel.

Following injection of the transfection mixture into the blood vessel of the avian embryo, the egg is sealed using a sufficient quantity of parafilm, or other suitable sealant film as known in the art. For example, where a 10 mm hole has been made in the shell, an approximately 20 mm square piece of parafilm may be used to cover the hole. A warm scalpel blade may then be used to affix the parafilm to the outer egg surface. Eggs are then turned over to the pointy-end down position and incubated at a temperature sufficient for the embryo to develop, such as until later analysis or hatch.

As used herein, the phrases "temperature sufficient for the embryo to develop" and "temperature sufficient for the embryo to develop into a chick" refer to incubation temperatures that are required for an avian embryo to continue to develop in the egg and preferably to develop into a chick that is ready to hatch. Suitable incubation temperatures can be determined by those of skill in the art. For example, a chicken egg is typically incubated at about 35.8 to about 38° C. Incubators are commercially available which control incubation temperate at desirable levels, for example, 37.9° C. at Days 1 to 6 post lay, about 37.6° C. at Days 9 and 10, about 37.5° C. at Days 11 and 12, about 37.4° C. at Day 13, about 37.3° C. at Days 14 and 15, about 37.2° C. at Day 16, about 37.1° C. at Day 17, and which may fall to about 35.8° C. by Day 22.

Genomic Integration of Polynucleotides

To facilitate integration of the polynucleotide into the genome of the avian germ cells, preferably a transposon, zinc finger nuclease, or other non-viral construct or vector is used in the method of the invention.

Examples of suitable transposons include Tol2 (Kawakami et al., 2002), mini-Tol2, Sleeping Beauty (Ivics et al., 1997), PiggyBac (Ding et al., 2005), Mariner and Galluhop. The Tol2 transposon which was first isolated from the medaka fish *Oryzias latipes* and belongs to the hAT family of transposons is described in Kawakami et al. (2000). Mini-Tol2 is a variant of Tol2 and is described in Balciunas et al. (2006). The Tol2 and Mini-Tol2 transposons facilitate integration of a transgene into the genome of an organism when co-acting with the Tol2 transposase. By delivering the Tol2 transposase on a separate non-replicating plasmid, only the Tol2 or Mini-Tol2 transposon and transgene is integrated into the genome and the plasmid containing the Tol2 transposase is lost within a limited number of cell divisions. Thus, an integrated Tol2 or Mini-Tol2 transposon will no longer have the ability to undergo a subsequent transposition event. Additionally, as Tol2 is not known to be a naturally occurring avian transposon, there is no endogenous transposase activity in an avian cell, for example a chicken cell, to cause further transposition events. As would be understood in the art, an RNA encoding the Tol2 transposase may be included in the transfection mixture as an alternative to a DNA plasmid encoding the transposase. Thus, the Tol2 transposon and transposase are particularly suited to use in the methods of the present invention.

Any other suitable transposon system may be used in the methods of the present invention. For example, the transposon system may be a Sleeping Beauty, Frog Prince or Mos1 transposon system, or any transposon belonging to the tc1/mariner or hAT family of transposons may be used.

The skilled person will understand that it may be desirable to include additional genetic elements in the constructs to be injected into the avian embryo. Examples of an additional genetic element which may be included in the nucleic acid construct include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, or drug resistance.

Genome editing technologies may also be used in the methods of the invention. By way of example, the genome editing technology may be a targeting nuclease. As used herein, the term "targeting nuclease" includes reference to a naturally-occurring protein or an engineered protein. In one embodiment, the targeting endonuclease may be a meganuclease. Meganucleases are endodeoxyribonucleases characterized by long recognition sequences, i.e., the recognition sequence generally ranges from about 12 base pairs to about 40 base pairs. As a consequence of this requirement, the recognition sequence generally occurs only once in any given genome. Among meganucleases, the family of homing endonucleases named LAGLIDADG has become a valuable tool for the study of genomes and genome engineering. A meganuclease may be targeted to a specific chromosomal sequence by modifying its recognition sequence using techniques well known to those skilled in the art.

In another embodiment, the "targeting nuclease" is a Zinc-finger nuclease. Zinc-finger nucleases (ZFNs) are artificial nucleases generated by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to precisely alter the genomes of higher organisms. Zinc finger nucleases are known in the art and described in, for example, U.S. Pat. No. 7,241,574 and reviewed in Durai et al. (2005) and Davis and Stokoe (2010).

Prior to the present invention, it was expected that in order to modify PGCs using zinc finger nuclease technology, zinc finger constructs would be introduced into cultured PGCs. Transfected cells comprising the desired insertion/modification would then be selected and cloned. The sorted and cloned cells would be injected into a PGC depleted recipient embryo.

The present inventors have found, surprisingly, that direct injection of a zinc finger nuclease construct into an avian embryo resulted in a specific genomic modification that could be detected in the gonad of the transfected embryo at Day 14. This finding was surprising because it was expected that the combined levels of efficiency of the transfection and zinc finger nuclease activity would be too low to detect a specific modification in a directly injected embryo. In view of the specificity of targeting desired DNA sequences, and the present inventors finding that the combination of a zinc finger nuclease and transfection reagent directly injected into an embryo achieving higher than expected levels of efficiency, zinc finger nucleases are particularly useful for introducing a polynucleotide into the genome of an avian germ cell in the methods of the present invention.

In yet another embodiment, the targeting endonuclease may be a transcription activator-like effector (TALE) nuclease (see, e.g., Zhang et al., 2011). TALEs are transcription factors from the plant pathogen *Xanthomonas* that can be readily engineered to bind new DNA targets. TALEs or truncated versions thereof may be linked to the catalytic domain of endonucleases such as Fok1 to create targeting endonuclease called TALE nucleases or TALENs.

In yet another embodiment, the "targeting nuclease" is a Clustered Regularly Interspersed Short Palindromic Repeats (CRISPR) nuclease (Barrangou, 2012). CRISPR is a microbial nuclease system involved in defence against invading phages and plasmids. CRISPR loci in microbial hosts contain a combination of CRISPR-associated (Cas) genes as well as non-coding RNA elements capable of programming the specificity of the CRISPR-mediated nucleic acid cleavage. Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer).

The Type II CRISPR is one of the most well characterized systems (for example, see Cong et al., 2013) and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. The CRISPR system can also be used to generate single-stranded breaks in the genome. Thus the CRISPR system can be used for RNA-guided site specific genome editing.

Polynucleotides

The methods of the present invention can be utilised to incorporate polynucleotides into the genome of avian primordial germ cells that can be transmitted to genetically modified progeny. The polynucleotides integrated into the genome may impart a desirable function or activity on the genetically modified cells comprising the polynucleotide, such as, for example, modifying a production trait or increasing disease resistance. Thus, polynucleotides that may be integrated into the genome of germ cells include those encoding short interfering RNAs (siRNAs), short-hairpin RNAs (shRNAs), extended short hairpin RNAs (ehRNAs), catalytic RNAs such as ribozymes, RNA decoys, as well as those encoding endogenous or exogenous polypeptides such as those that can be used to modulate a production trait or increase resistance to disease in an avian.

Thus, in some embodiments, the methods of the invention can be used to modify any trait of an avian species. Preferred traits which can be modified include production traits and disease resistance. As used herein, the term "production trait" refers to any phenotype of an avian that has commercial value such as muscle mass, sex, disease resistance or nutritional content. Preferred traits which can be modified according to the methods of the present invention include sex, muscle mass and disease resistance. Examples of genes that can be targeted to modify sex as a production trait in an avian include DMRT1, WPKCI (ASW), R-spondin, FOX9, aromatase, AMH and β-catenin.

As used herein, the term "muscle mass" refers to the weight of muscle tissue. An increase in muscle mass can be determined by weighing the total muscle tissue of a bird which hatches from an egg treated as described herein when compared to a bird from the same species of avian, more preferably strain or breed of avian, and even more preferably the same bird, that has not been administered with a nucleic acid as defined herein. Alternatively, specific muscles such as breast and/or leg muscles can be used to identify an increase in muscle mass. Genes that can be targeted for the modulation of muscle mass include, for example, the myostatin gene.

RNA Interference

In certain embodiments, the methods of the present invention utilise nucleic acid molecules encoding double-stranded regions for RNA interference in order to modulate traits in an avian. The terms "RNA interference", "RNAi" or "gene silencing" refer generally to a process in which a double-stranded RNA molecule reduces the expression of a nucleic acid sequence with which the double-stranded RNA molecule shares substantial or total homology. However, it has been shown that RNA interference can be achieved using non-RNA double stranded molecules (see, for example, US 20070004667).

The double-stranded regions should be at least 19 contiguous nucleotides, for example about 19 to 23 nucleotides, or may be longer, for example 30 or 50 nucleotides, or 100 nucleotides or more. The full-length sequence corresponding to the entire gene transcript may be used. Preferably, they are about 19 to about 23 nucleotides in length.

The degree of identity of a double-stranded region of a nucleic acid molecule to the targeted transcript should be at least 90% and more preferably 95-100%. The nucleic acid molecule may of course comprise unrelated sequences which may function to stabilize the molecule.

The term "short interfering RNA" or "siRNA" as used herein refers to a nucleic acid molecule which comprises ribonucleotides capable of inhibiting or down regulating gene expression, for example by mediating RNAi in a sequence-specific manner, wherein the double stranded portion is less than 50 nucleotides in length, preferably about 19 to about 23 nucleotides in length. For example the siRNA can be a nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siRNA can be assembled from two separate oligonucleotides, where one strand is the sense strand and the other is the antisense strand, wherein the antisense and sense strands are self-complementary.

As used herein, the term siRNA is meant to be equivalent to other terms used to describe nucleic acid molecules that are capable of mediating sequence specific RNAi, for example micro-RNA (miRNA), short hairpin RNA (shRNA), short interfering oligonucleotide, short interfering nucleic acid (siNA), short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siRNA molecules as described herein can be used to epigenetically silence genes at both the post-transcriptional level or the pre-transcriptional level. In a non-limiting example, epigenetic regulation of gene expression by siRNA molecules as described herein can result from siRNA mediated modification of chromatin structure to alter gene expression.

By "shRNA" or "short-hairpin RNA" is meant an RNA molecule where less than about 50 nucleotides, preferably about 19 to about 23 nucleotides, is base paired with a complementary sequence located on the same RNA molecule, and where said sequence and complementary sequence are separated by an unpaired region of at least about 4 to about 15 nucleotides which forms a single-stranded loop above the stem structure created by the two regions of base complementarity.

Included shRNAs are dual or bi-finger and multi-finger hairpin dsRNAs, in which the RNA molecule comprises two or more of such stem-loop structures separated by single-stranded spacer regions.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression.

Disease Resistance

The methods of the present invention may be used to integrate a polynucleotide that confers disease resistance upon a cell into the genome of primordial germ cells in an avian embryo. For example, the polynucleotide may encode a nucleic acid molecule such as an siRNA, shRNA or miRNA that reduces the expression of a host or pathogen gene resulting in a decrease in viral replication in cells in which the polynucleotide is present. "Virus replication" as used herein refers to the amplification of the viral genome in a host cell, the packaging of the viral genome in a cell and/or the release of infectious viral particles from a cell.

Alternatively, the polynucleotide may encode an RNA decoy. RNA decoys are known in the art and contain particular nucleotide base sequences which bind virus proteins which are essential for the replication of a pathogenic virus. RNA decoys targeting HIV proteins were first described by Sullenger et al. (1990). The skilled person will appreciate, however, that RNA decoys may be designed to target proteins that play a role in the replication of avian viral pathogens, such as RNA decoys targeting the polymerase complex proteins of the influenza virus.

Preferably, by reducing virus replication in avian cells, the genetically modified avian comprising the polynucleotide will have an increased resistance to a viral pathogen. As used herein, an avian that is "resistant" or has "increased resistance" to a pathogen or viral pathogen exhibits reduced or no symptoms of disease compared to a susceptible avian when exposed to the pathogen. Using the methods of the invention, avians can be made resistant to pathogens such as, but not limited to, influenza virus, Marek's disease virus, Newcastle Disease virus and Infectious Bursal Disease Virus.

In Ovo Production of Recombinant Proteins

Petitte and Modziak (2007) describe the domestic hen as a "very efficient protein bioreactor". Recognizing that the avian egg contains large amounts of protein, and over half of the protein in egg white or albumin is composed of a single species, there is great potential in producing recombinant or heterologous proteins in eggs. Difficulties encountered in prior art methods of producing transgenic poultry for the production of therapeutic proteins in eggs are well described in the art. Although achieved using an undesirable lentivirus system, the production of transgenic birds that deposit high levels of commercially relevant proteins in an egg has been achieved. Accordingly, the methods of the present invention may be used to produce genetically modified avians that express a heterologous or recombinant polypeptide in eggs. Proteins of commercial importance that could be produced in eggs include therapeutic proteins such as antibodies and vaccine antigens.

Production and Breeding of Genetically Modified Avians

The methods of the present invention include methods of breeding genetically modified avians and methods of producing food from genetically modified avians. The skilled person will appreciate that an avian of the invention comprising genetically modified germ cells may be germline chimeric, in that only some of the germ cells that have migrated into the gonads are genetically modified. Thus, the avian comprising genetically modified germ cells can be bred to produce progeny in which all cells are genetically modified. Thus in one embodiment, the invention provides a method for producing a genetically modified avian, the method comprising: (i) obtaining the avian comprising germ cells genetically modified according to the invention (ii) breeding from the avian comprising genetically modified germ cells to produce progeny, and (iii) selecting progeny comprising the polynucleotide inserted into the genome.

The avian comprising genetically modified germ cells of the invention, and the genetically modified avian according to the invention, may be used in the production of food. Thus, the methods of the invention are applicable to the production of poultry products for human and animal consumption. Methods of producing food from poultry are well known in the art and may comprise the harvesting of meat and/or eggs from poultry such as, but not limited to, a chicken. In certain embodiments, the avian has been genetically modified to include a polynucleotide that modulates a production trait.

EXAMPLES

Example 1

Direct Injection of EGFP Expression Construct into Embryos 5.1 µg of a nucleic acid construct encoding enhanced GFP (EGFP) flanked by Tol2 sequences and 1.0 µg of a plasmid encoding the Tol2 transposase were complexed with 3 µl Lipofectamine 2000. The complexing of the nucleic acids and transfection reagent were carried out in a total volume of 90 µl of OptiMEM or OptiPRO media using the incubation times recommended by the manufacturer (Life Technologies).

Following the final 20 minute incubation, 1-3 µm of the complex was injected into a blood vessel of Day 2.5 chicken embryos (Stages 13-17; Hamburger and Hamilton, 1951). No removal of blood was required. Access to the embryo was achieved by the removal of a small (10 mm) section of shell. After injection the hole was sealed with a 20 mm square of parafilm.

Figure 2:
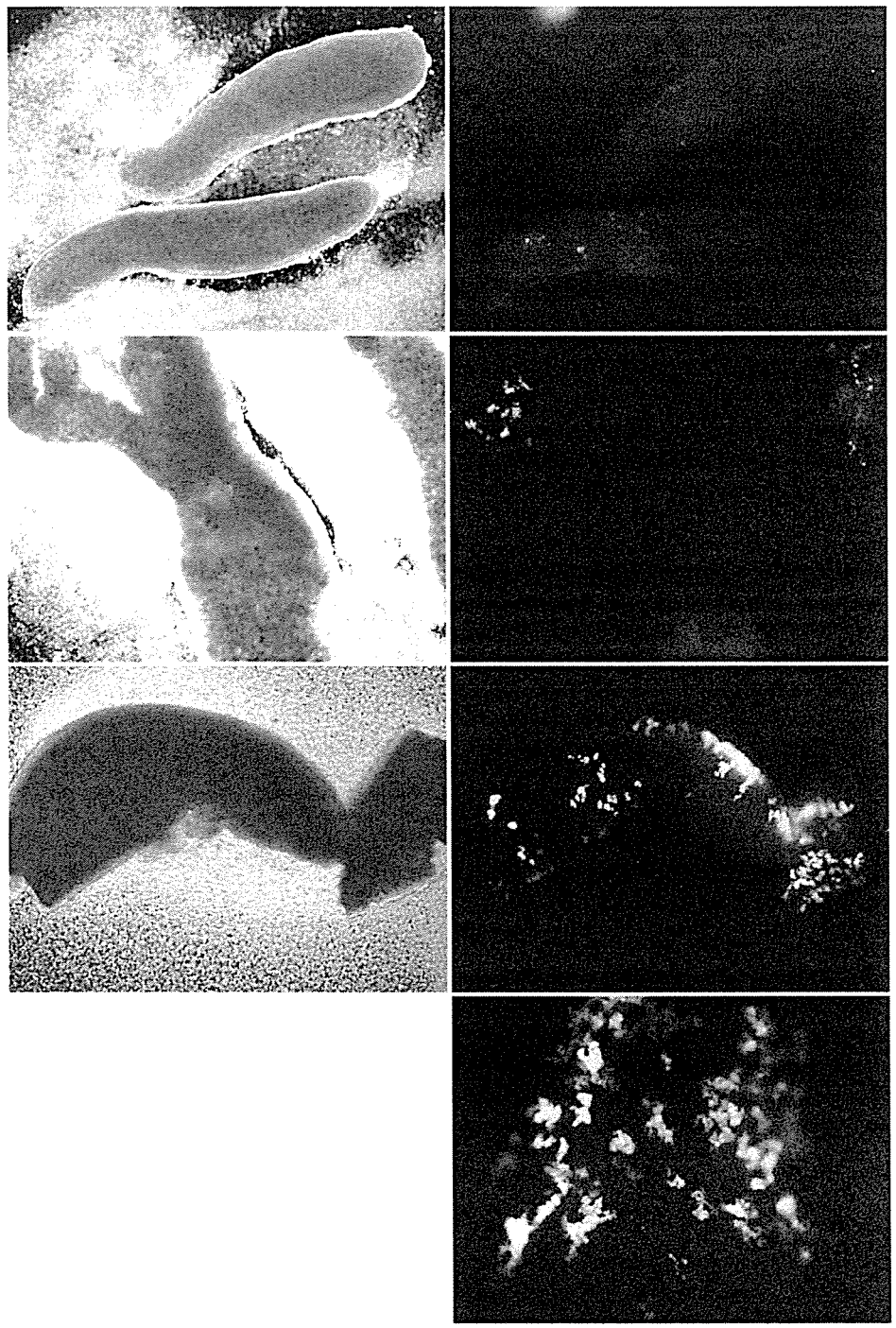
FIG. 2. Direct injection of DNA encoding EGFP complexed with Lipofectamine 2000 into avian embryos Day 14 images. Fluorescent (right side) and matching brightfield (left side) images of gonads removed from Day 14 embryos. Last fluorescent image is a close-up from the left hand cluster of green cells in an embryo. This region was dissected away from the rest of the gonad for staining with chicken vasa homologue (cvh). A small section of the rest of the gonad was used as a negative control.
Figure 3:
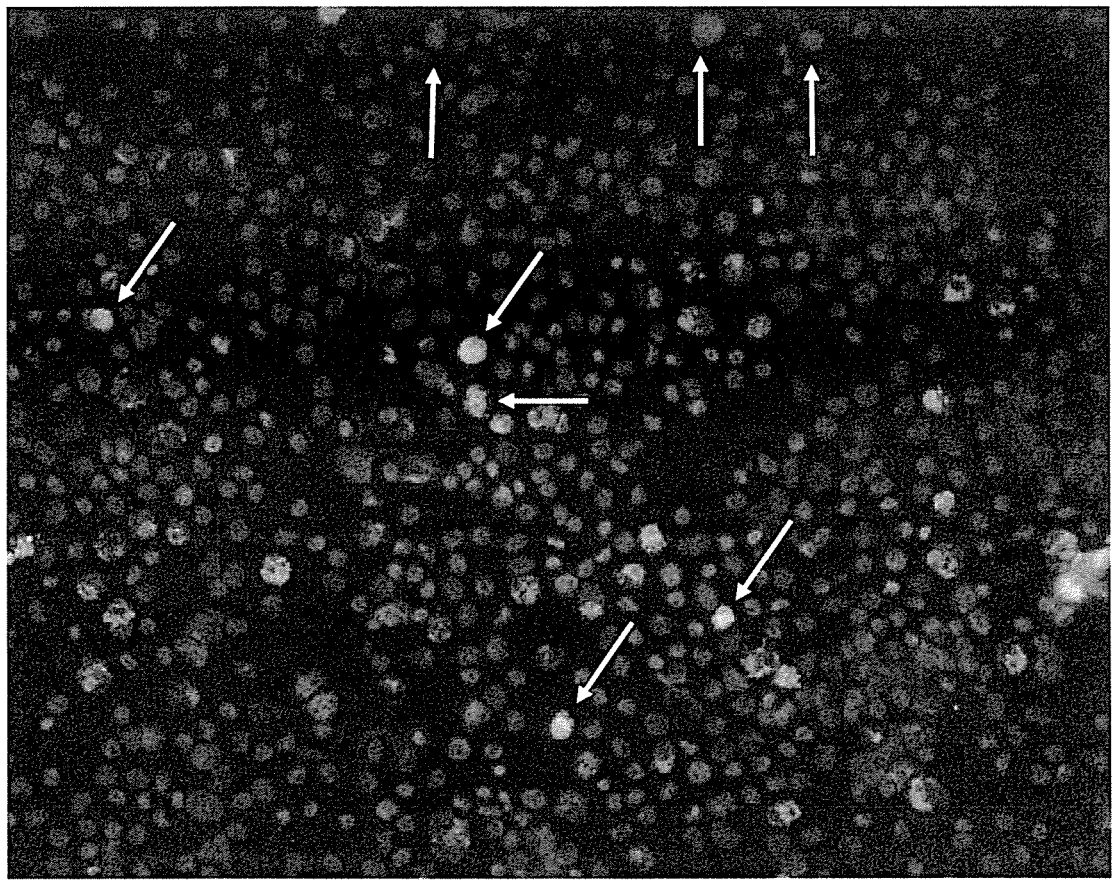
FIG. 3. Direct injection of DNA encoding EGFP complexed with Lipofectamine 2000 into avian embryos. Staining of cells for PGC marker cvh. DAPI stain showing nuclear material and staining of all cells. cvh, a PGC specific marker has stained a subpopulation of cells (lighter grey cells). Transformed cells that have received the transposon through direct injection and stained green are indicated by arrows.

EGFP expression was observed at Day 7 and Day 14 in most gonads at varying levels. Cells dissociated from gonads and green cells also shown to be PGCs (FIGS. 1, 2 and 3).

Example 2

In Vitro Optimisation of DNA to Transfection Reagent Ratios

Experiments were undertaken to test the optimal ratio of DNA:Lipofectamine 2000 and the volume of the media to make up the transfection complex. A DNA construct encoding EGFP and a single hairpin (shRNA) with flanking Tol2 sequences was complexed with Lipafectamine 2000 in OptiMEM volumes of 50, 40, 30 or 20 µl. The ratios of DNA (µg) to Lipofectamine 2000 (µl) used were as follows: 1:2, 2:4 and 4:8.

The complexes were transfected into chicken fibroblast (DF-1) cells and analysed fro the expression of EGFP. Results indicated (not shown) that a ratio of DNA (µg): Lipofectamine 2000 of 1:2 in 30 µm medium worked slightly better than a ratio of 2:4 in 50 µl.

Figure 4:
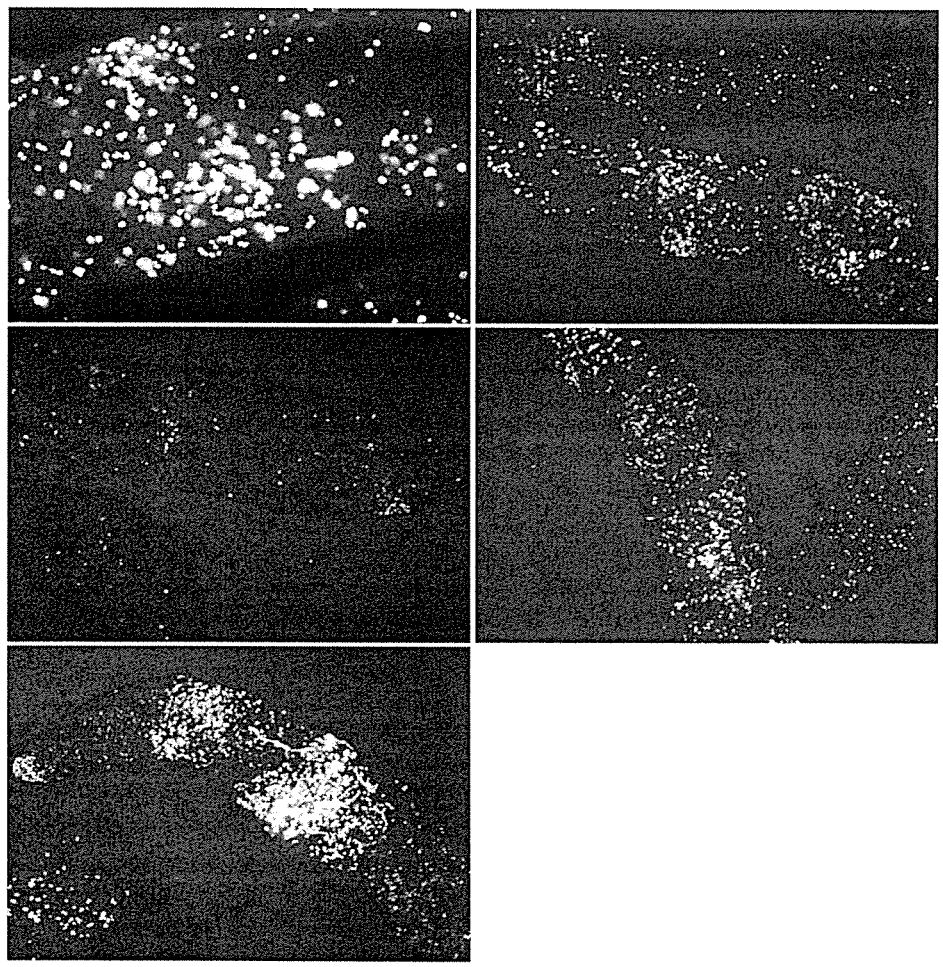
FIG. 4. Confirmation of in vitro optimization by Direct Injection into avian embryos. EGFP expression in gonads of Day 14 embryos.

The in vitro data was subsequently confirmed in embryos. 0.33 µg of DNA construct comprising the Tol2 transposon, 0.66 µg transposase plasmid, and 2 µl Lipofectamine 2000 were complexed in OptiMEM and injected directly into chicken embryos. All living embryos had good levels of EGFP expression at Day 14 (FIG. 4).

Example 3

Testing FuGene Transfection Reagent

FuGene (Promega) was tested as a transfection reagent using a DNA:Fugene ratio similar to that recommended by the manufacturer for cell culture transfection. The DNA construct complexed with FuGene comprised an EGFP expression cassette with flanking Tol2 sequences. The complex (0.66 µg of the EGFP-Tol2 construct, 1.33 µg transposase plasmid, 6 µl FuGene) was injected directly into 15 embryos. One of the embryos showed very small amounts of EGFP expression in the gonads at Day 14. This experiment was repeated, and at Day 12 all 10 embryos that were injected were still alive. Two of the embryos had a couple of green cells in the gonads.

Example 4

Direct Injection Transformation of Broiler Lines

As the previous direct injection experiments had been performed on chicken egg layer lines, the purpose of this experiment was to test whether the direct injection method could be used to successfully transform chicken broiler lines. An EGFP expression construct comprising a single hairpin and flanking Tol2 sequences was complexed with Lipofectamine 2000 (0.33 µg transposon construct, 0.66 µg transposase, 2 µl Lipofectamine 2000) and injected directly into the dorsal aorta of chicken embryos. Twelve out of 13 embryos injected were alive at Day 10 and good amounts of EGFP expression were detected in most gonads.

Figure 5:
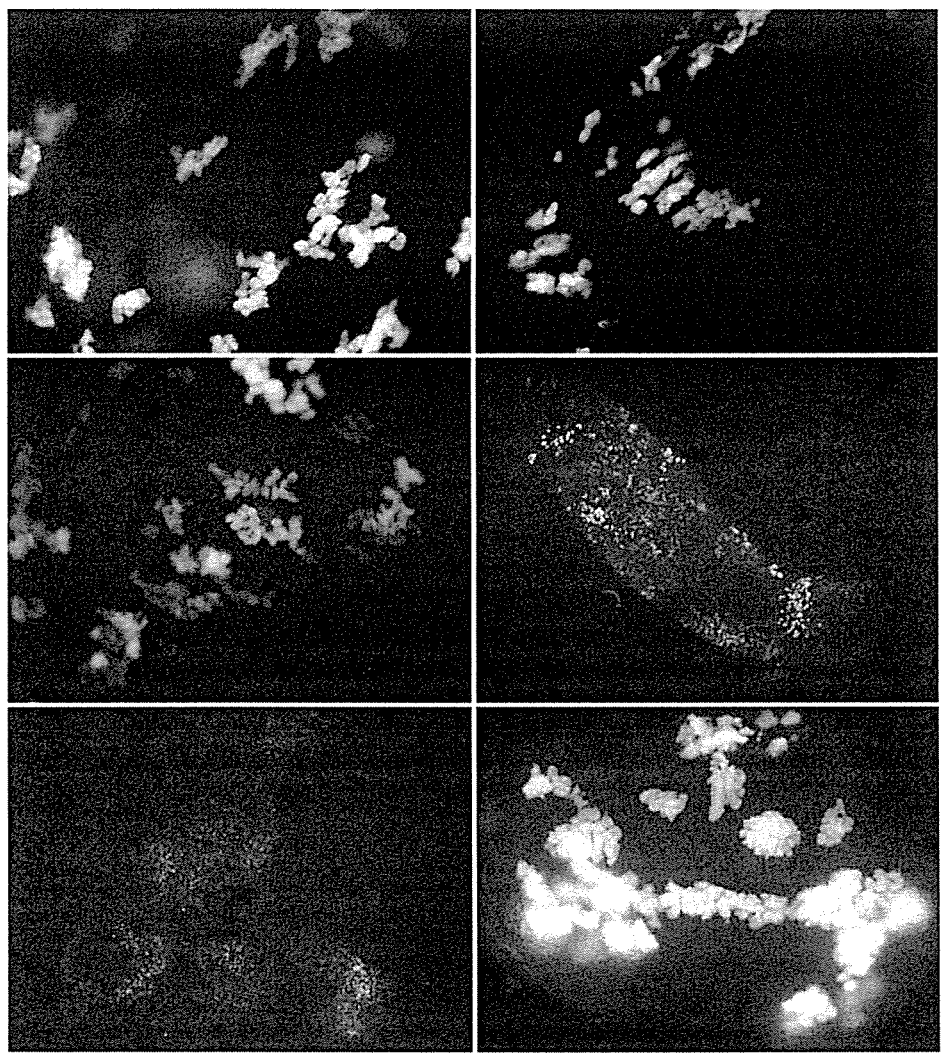
FIG. 5. Direct injection of DNA encoding EGFP and a multi-warhead construct comprising multiple sequences encoding shRNAs complexed with Lipofectamine 2000 into chicken broiler line embryos. Fluorescent images from Day 12 gonads.
Figure 6:
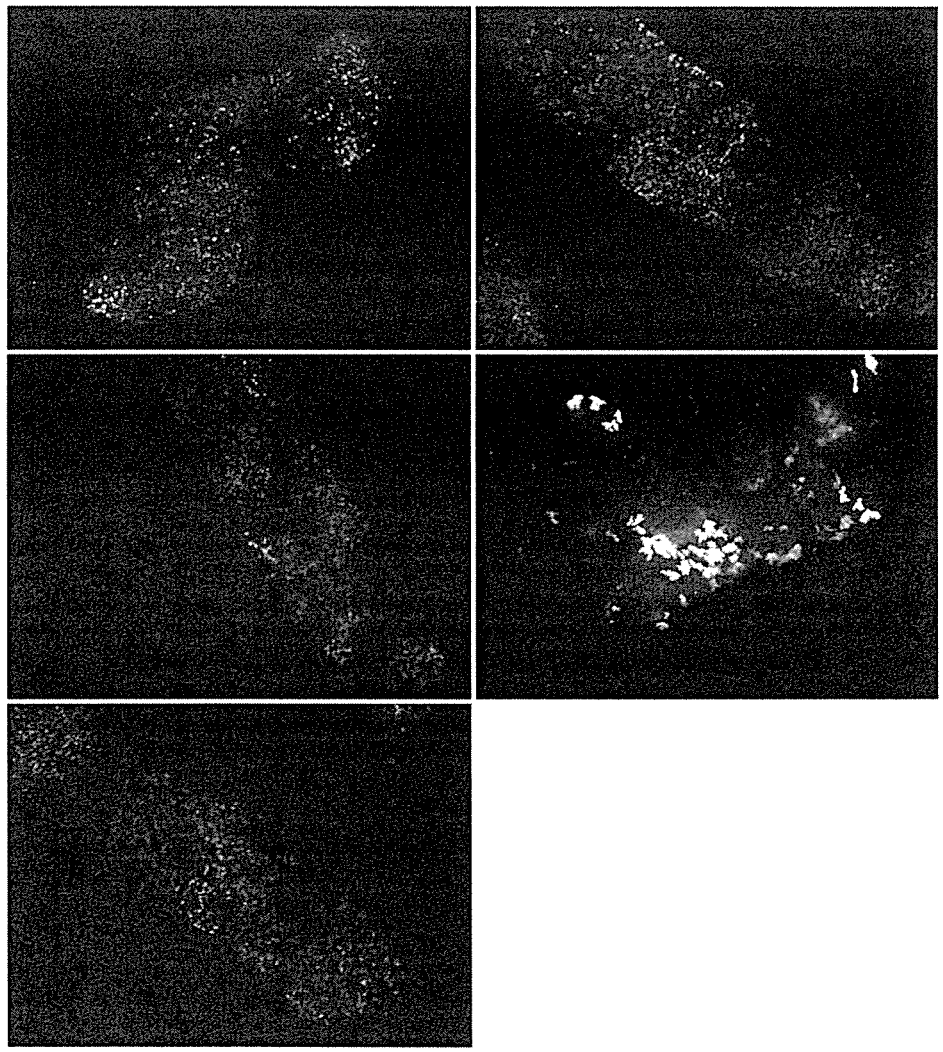
FIG. 6. Direct injection of DNA encoding EGFP, a multi-warhead construct and extended hairpin construct complexed with Lipofectamine 2000 into chicken layer line embryos. Fluorescent images of the gonads of Day 14 Embryos after Direct Injection.

This experiment was repeated with an EGFP expression construct comprising multiple hairpins (shRNAs) (0.33 µg of transposon, 0.66 µg transposase, 2 µl Lipofectamine 2000). Good amounts of EGFP expression were found in Day 12 embryos (FIG. 5).

Example 5

Comparison of OptiMEM with OptiPRO as Transfection Reagent Media

A comparison was made between OptiMEM (containing animal products), OptiPRO (contains no animal products), and PBSA as the transfection reagent media. An EGFP expression construct comprising flanking Tol2 sequences was complexed with transfection reagent (0.33 µg of transposon, 0.66 µg transposase, 2 µl Lipofectamine 2000) and injected directly into chicken embryos. All of the embryos showed some green in the gonads at Day 12 and the media used did not affect mortality. OptiMEM and OptiPRO gave equivalent results, whereas PBSA resulted in a significantly reduced expression of EGFP in gonads.

Example 6

Chicken Layer Lines Injected with Multi-Warhead Construct

Two DNA constructs were complexed with transfection reagent and injected directly into chicken embryos. The first DNA construct comprised an EGFP expression cassette and multiple shRNA hairpins flanked by Tol2 sequences, and the second construct comprised an EGFP expression construct and a single extended hairpin cassette encoding three double-stranded regions. The constructs were complexed with transfection reagent in the following amounts: 0.33 µg of transposon, 0.66 µg transposase, 2 µL Lipofectamine 2000. At Day 14, EGFP expression was found in the gonads of most embryos for both constructs.

Example 7

Testing for Persistence of Tol2-EGFP

A DNA construct comprising an EGFP expression cassette, multiple hairpins and flanked by Tol2 were complexed with transfection reagent. (0.33 µg of transposon, 2 µL Lipofectamine 2000). The transfection complex without transposase was injected directly into chicken embryos.

Embryos where transposase was omitted still showed green cells in some embryos, but in fewer cells than seen when transposase is included. This suggests that plasmid can remain in gonadal cells for at least 2 weeks after direct injection and that not all green observed is due to Tol2 integration into the genome.

Example 8

Animal-Free Lipofectamine

Figure 7:
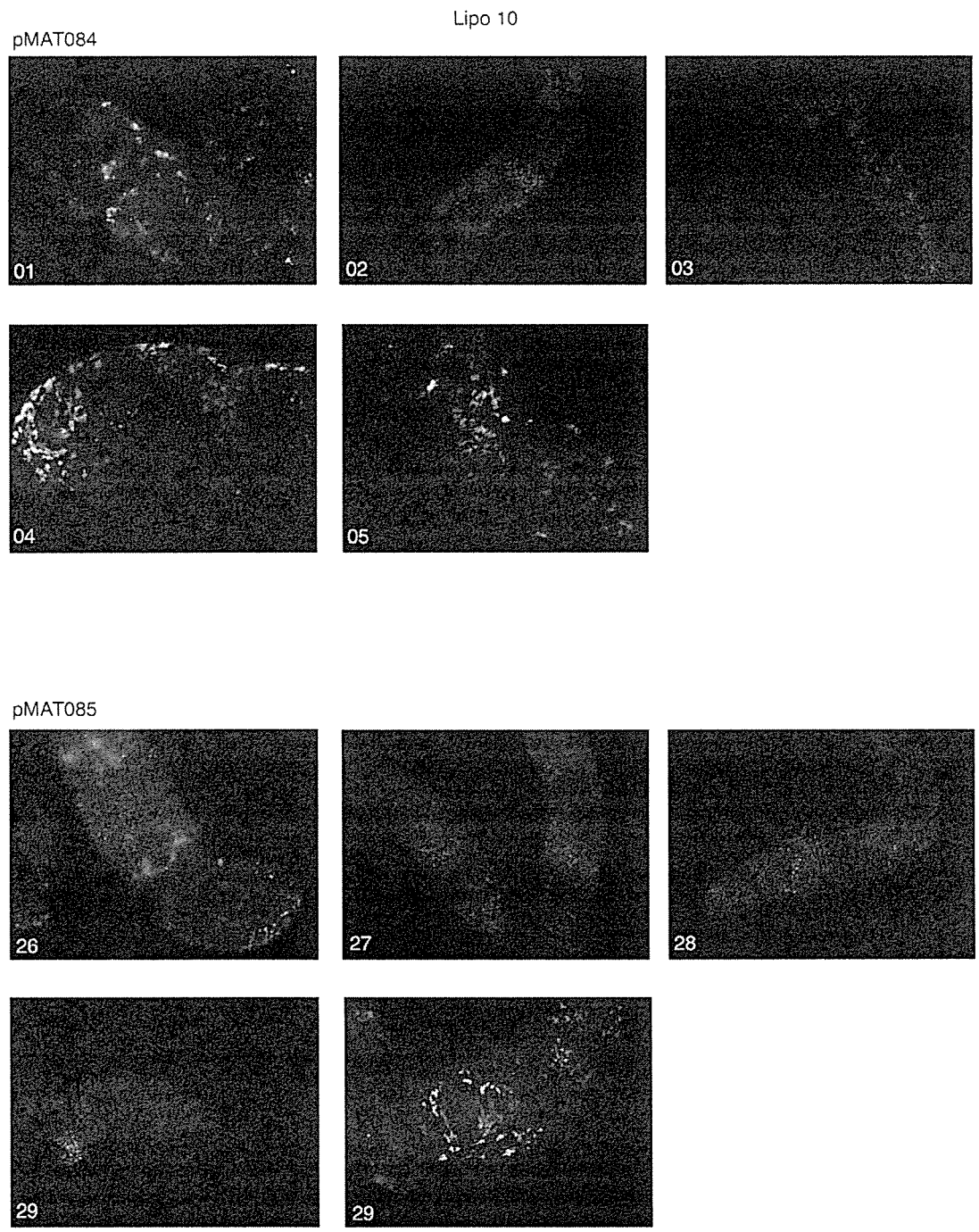
FIG. 7. Direct injection of Tol2-EGFP construct with each of two multiple shRNA expression cassettes (pMAT084 and pMAT085). Images of 10 gonads taken at Day 14 showing EGFP expression.

An EGFP expression cassette with Tol2 and multiple shRNA expression cassettes was complexed with animal-product free transfection reagent (Lipofectamine 2000CD) (0.33 µg of transposon, 0.66 µg transposase, 2 µl Lipofectamine 2000 CD). At Day 14 all 10 embryos examined had good amounts of EGFP expression in the gonads (FIG. 7).

Example 9

Direct Injection at Day 3.5

In all previous experiments, injections of transfection complexes were performed at Day 2.5. The purpose of this experiment was to test an alternative time (Day 3.5) for direct injection of embryos. A DNA construct comprising an EGFP expression construct and Tol2 was complexed with Lipofectamine 2000CD (0.33 µg of transposon, 0.66 µg transposase, 2 µl Lipofectamine2000 CD).

At Day 14, 8 of 21 embryos had small amounts of EGFP expression in the gonads. Thus, the timing of the direct injection at Day 2.5 is important, and by Day 3.5 efficient transfection of the PGCs is not observed.

Example 10

Altering the Proportions of Transposon to Transposase

While maintaining the DNA:Lipofectamine2000 CD:media ratios, we increased the proportion of transposon in the DNA mix while slightly decreasing the transposase plasmid proportion. Slightly different volumes were used due to the need to inject more eggs in future experiments. The inventors also tested removing blood from the embryo before injection of the transfection mixture to determine if this allowed an increased volume of the mixture to be injected.

A DNA construct comprising an EGFP expression cassette and Tol2 was complexed with transfection reagent. (0.66 µg of transposon, 1.0 µg transposase, 3 µl Lipofectamine2000 CD). At Day 14 the pre-bleeding embryos had similar levels of EGFP expression in the gonads compared with the non pre-bleed embryos. The new DNA ratios worked well with good levels of EGFP expression being observed.

Example 11

JetPEI Transfection Reagent

For JetPEI, the DNA construct comprising an EGFP expression cassette and Tol2 was complexed with transfection reagent (4 µg of transposon, 6 µg transposase, 1.6 µl JetPEI (Polyplus transfection) in 50 µm OptiPRO (with 5% glucose). JetPEI caused the blood to clot upon injection, but this did not affect embryo survivability. Green cells were found in these embryos and in the gonads but the majority were morphologically different to the transformed PGCs seen when Lipofectamine2000 was used.

A second experiment was performed to test the JetPEI transfection reagent. Two reaction mixes were used: i) 0.66 µg of transposon, 1.0 µg transposase, 0.5 µl JetPEI in 100 µl OptiPRO (with 5% glucose); and ii) 1.32 µg of transposon, 2.0 µg transposase, 0.5 µl JetPEI in 100 µl OptiPRO (with 5% glucose).

JetPEI caused the blood to clot upon injection and reaction mix (ii) resulted in improved embryo survivability. Again, some EGFP expression was found in the gonads but again the cell type did not appear to be PGC-like. Gonads were taken and cells dissociated and stained for PGC markers. No green cells showed staining for the PGC markers confirming that PGCs were not being transfected by the JetPEI complex.

Example 12

Zinc Finger Nuclease

The purpose of the experiment was to determine whether Zinc-finger nuclease plasmids can be used to transform PGCs by the direct injection technique. The DNA used in the experiment comprised two zinc-finger nuclease plasmids and the overlapping fragment, which was complexed with transfection reagent 0.5 µg of each plasmid, 3 µl Lipofectamine2000 CD, in 90 µl OptiPRO.

As there was no EGFP present on the plasmids, the inventors relied on a PCR test that would amplify a fragment only if the overlapping fragment has been incorporated into the chicken genome. After 14 days of incubation, gonads were removed, PGCs enriched using an antibody sorting method, and genomic DNA prepared. PCR revealed that the overlapping fragment had been incorporated into the chicken genome. These results demonstrate that Zinc-finger nucleases are suitable for integrating DNA into the genome of avian PGCs using the direct injection method of the present invention.

Example 13

Results

Following the protocols outlined above, the inventors saw significant transformation of PGCs in the gonads of recipient embryos, and to a much higher degree than described in prior art methods of transfecting PGCs. Through staining of cells with PGC-specific markers the inventors showed that the majority of cells transformed in the gonad were PGCs. The inventors have raised recipient embryos to sexual maturity and have been able to detect Tol2 transposon sequences in the semen of >90% of the adult males.

Other transfection reagents were used, however the lipid-based reagents gave superior transfection of PGCs. JetPEI did transfect cells by this method but it could not be shown that any of the transfected cells were PGCs. FuGene transfected cells at a very low rate.

Example 14

Direct Injection Modification of the Genome Using Zinc Finger Nucleases

A zinc finger nuclease (ZFN) which targets a region of intron 5 of the PANK1 gene was injected along with a plasmid containing the anti-influenza shRNA PB1-2257 and the regions required for homologous repair into embryos which were subsequently analysed for integration of the shRNA.

A total of 1.5 µg of DNA (500 µg of each ZFN plasmid and 500 µg of the repair plasmid) was added to 45 µl of OptiPRO and then complexed with 3 µl of lipofectamine2000 CD in 45 µl of OptiPRO prior to being injected into 30 day 2.5 eggs. The eggs where incubated until day 7 when the gonads were removed, disassociated and PGC's enriched for using a MACS sort with a SSEA-1 Antibody (Santa Cruz Biotech). DNA was extracted from the PGC enriched sample from the ZFN treated embryos and control embryos using a Qiagen DNAeasy kit.

A PCR to screen for successful integration of the shRNA was carried out using a primer which binds to the genome outside the region used for homologous repair (Screen 7 5' GTGACTCAGACTCCTGTTAG (SEQ ID NO:3)) and one which binds to the shRNA (Screen 6 5' TCTGCTGCTTCACAGTCTTC (SEQ ID NO:4)). PCR was performed using green master mix (Promega) following the manufactures instructions using cycling conditions of 94° C. for 2 min followed by 36 cycles of 94° C. for 45 secs, 55° C. for 45 secs and 72° C. for 1 min 10 sec. This was followed by a final extension at 72° C. for 10 min.

Figure 8:
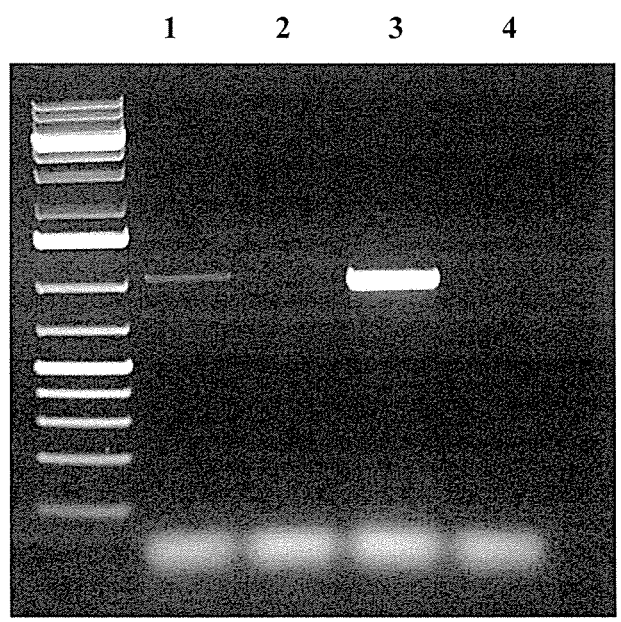
FIG. 8. Gel electrophoresis of screening PCR products indicating integration of the PB shRNA into the direct injected embryos. DNA was extracted from a PGC enriched sample from the ZFN treated embryos as well as from control embryos at 5 days post direct injection with ZFN and a repair plasmid (containing the PB shRNA). A screening PCR was then performed to detect integration of the PB shRNA into the genome. Lane 1 shows PB injected embryos, lane 2 Control embryos, lane 3 ZFN treated cells (positive control) and lane 4 is a water control.

PCR was carried out on the DNA PGC enriched sample from the ZFN treated embryos as well as from control embryos, DNA from positive control cells, which have been previously shown to have the shRNA integrated into them and a water control. FIG. 8 shows the gel electrophoresis of these PCR reactions. The first lane, which contains the PCR from the ZFN direct injected embryos, clearly shows a band indicating genomic integration in the embryos that were injected.

Example 15

Results of Direct Injection Genome Modification of Chickens

After a number of rounds of direct injections, a total of 277 roosters where raised to sexual maturity and their semen tested for presence of the Tol2 transgene. Of the 277 samples tested 98 were found to contain the Tol2 transgene with varying levels of percentage positive semen. A number of these positive G(0) roosters were put into matings and a total of 7393 G(1) chicks were screened. Sixty-five of the chicks were found to be transgenic. Subsequent matings using these G(1) chicks have shown Mendelian inheritance of the transgenes to the G(2) generation.

Hatched chicks were grown to sexual maturity and quantitative real time PCR (qPCR) was used to detect the presence of miniTol-EGFP in the semen. Semen samples were collected and DNA was extracted from 20 µl of semen diluted in 180 µl of PBS using the Qiagen DNeasy Blood and Tissue Kit following the manufactures instructions. The semen genomic DNA was then diluted 1/100 in ddH$_2$O for use in the PCR reaction. qPCR was carried out on a Mastercycler® ep realplex (Eppendorf Hamburg, Germany) following the manufactures instructions. In short, 20 µl reactions were set up containing 10 µl of Taqman 2× Universal master mix (Applied Biosystems), 1 µl 20×FAM labeled Assay Mix (Applied Biosystems) and 9 µl of diluted DNA. Each sample was set up in duplicate with specific primers and probe for minTol2:

```
Fwd primer
                                    (SEQ ID NO: 5)
5' CAGTCAAAAAGTACTTATTTTTTGGAGATCACT 3'

Reverse primer
                                    (SEQ ID NO: 6)
5' GGGCATCAGCGCAATTCAATT 3';

Detection probe
                                    (SEQ ID NO: 7)
5' ATAGCAAGGGAAAATAG 3';
``` and specific primers and probe for a genomic control region from the chicken genome which acts as a template control:

```
Forward primer
                                    (SEQ ID NO: 8)
5' GATGGGAAAACCCTGAACCTC 3';

Reverse primer
                                    (SEQ ID NO: 9)
5' CAACCTGCTAGAGAAGATGAGAAGAG 3';

Detection probe
                                    (SEQ ID NO: 10)
5' CTGCACTGAATGGAC 3'.
```

The PCR cycle parameters were an Initial denaturing step at 95° C. for 10 minutes followed by 45 cycles of 95° C. for 15 seconds and 60° C. for 1 minute. Each rooster was tested at least twice and was classified positive if a $C_T$ value of less than 36 was obtained for minTol2. A $C_T$ of less than 32 for the control genomic region was used to indicate there was sufficient DNA in the sample tested.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

The present application claims priority from U.S. 61/636,331 filed 20 Apr. 2012, U.S. 61/783,823 filed 14 Mar. 2013 and AU 2013204327 filed 12 Apr. 2013, the entire contents of each of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Balciunas et al. (2006) PLoS Genet. 10:e169.
Barrangou (2012) Nature Biotechnology, 30:836-838.
Cong et al. (2013) Science, 339:819-823.
Davis and Stokoe (2010) BMC Med, 8:42.
Ding et al. (2005) Cell, 122:473-483.
Durai et al. (2005) Nucleic Acids Res, 33:5978-5990.
Hamburger and Hamilton (1951) J Morphol, 88:49-92.
Haensler and Szoka, (1993) Bioconjugate Chem, 4:372-379.
Ivics et al. (1997) Cell, 91:501-510.
Kagami et al. (1997) Mol Reprod Dev, 48:501-510.
Kawakami et al. (2000) Proc Natl Acad Sci USA, 97:11403-11408.
Petitte (2002) J Poultry Sci, 39:205-228.
Pettite and Modziak (2007) Proc Natl Acad Sci USA, 104:1739-1740.
Sullenger et al. (1990) Cell, 63:601-608.
Tang et al. (1996) Bioconjugate Chem, 7:703-714.
Zhang et al. (2011) Nature Biotechnology, 29:149-153.

The invention claimed is:

1. A method for producing a chicken comprising germ cells whose genomes comprise a recombinant polynucleotide, the method comprising:
(i) injecting a transfection mixture comprising
   a) a plasmid comprising a recombinant polynucleotide encoding a marker protein flanked by Tol2 or mini-Tol2 sequences,
   b) a plasmid encoding a Tol2 transposase, and
   c) a cationic lipid, into a blood vessel of a Stage 12-17 chicken embryo contained in an egg, wherein the recombinant polynucleotide encoding a marker protein is inserted into the genome of one or more primordial germ cells in the chicken embryo by the transposase encoded in the plasmid of b); and
(ii) incubating the injected chicken embryo obtained in step (i) such that a chicken comprising germ cells whose genomes comprise the recombinant polynucleotide and express the marker protein is obtained.

2. The method of claim 1, wherein the Stage 12-17 chicken embryo is a Stage 13-14 chicken embryo.

3. The method of claim 1, wherein the cationic lipid is a monovalent cationic lipid selected from one or more of DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethylhydroxy ethyl ammonium bromide) and DDAB (dimethyl dioctadecyl ammonium bromide).

4. The method of claim 1, wherein the cationic lipid is a polyvalent cationic lipid selected from one or more of DOSPA (2,3-dioleyloxy-N-[2(sperminecarboxamido)ethyl]-N,N-dimethyl-1-propanaminium trifluoroacetate), DOSPER (1,3-dioleoyloxy-2-(6carboxy spermyl)-propyl-amid, TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldiolspermine).

5. The method of claim 1, wherein the transfection mixture further comprises a neutral lipid.

6. The method of claim 5, wherein the neutral lipid comprises dioleoyl phosphatidylethanolamine (DOPE), diphytanoylphosphatidylethanolamine (DPhPE) or cholesterol.

7. The method of claim 1, which further comprises:
(iii) allowing the chick, or progeny thereof, to develop into a sexually mature chicken comprising germ cells whose genomes comprise the recombinant polynucleotide encoding a marker protein, and
(iv) mating the sexually mature chicken with another chicken to produce progeny whose genomes comprise the recombinant polynucleotide encoding a marker protein.

8. The method of claim 1, wherein the plasmid comprising a recombinant polynucleotide is flanked by Tol2 sequences.

* * * * *